(12) United States Patent
McKeen et al.

(10) Patent No.: US 10,345,205 B2
(45) Date of Patent: Jul. 9, 2019

(54) FLUID SAMPLE PREPARATION SYSTEMS AND METHODS

(71) Applicant: Roche Diagnostics Hematology, Inc., Westborough, MA (US)

(72) Inventors: Brian J. McKeen, Bow, NH (US); Eric D. Yeaton, Epsom, NH (US); James L. Dowling, Milford, NH (US); David Zahniser, Wellesley, MA (US); Stephen Conroy, Maynard, MA (US)

(73) Assignee: Roche Diagnostics Hematology, Inc., Brighton, MA (US)

( * ) Notice: Subject to any disclaimer, the term of this patent is extended or adjusted under 35 U.S.C. 154(b) by 0 days.

(21) Appl. No.: 15/450,731

(22) Filed: Mar. 6, 2017

(65) Prior Publication Data

US 2017/0241875 A1    Aug. 24, 2017

Related U.S. Application Data

(60) Continuation of application No. 14/738,257, filed on Jun. 12, 2015, now Pat. No. 9,588,026, which is a
(Continued)

(51) Int. Cl.
*G01N 1/30* (2006.01)
*G01N 35/10* (2006.01)
(Continued)

(52) U.S. Cl.
CPC ............... *G01N 1/312* (2013.01); *G01N 1/30* (2013.01); *G01N 35/00029* (2013.01);
(Continued)

(58) Field of Classification Search
CPC ............ B23B 5/02; G01N 1/312; G01N 1/30
See application file for complete search history.

(56) References Cited

U.S. PATENT DOCUMENTS 4,169,125 A    9/1979 Rodriguez et al.
4,533,643 A *  8/1985 Bell .................... B01D 11/0207
                                                 422/502
(Continued)

FOREIGN PATENT DOCUMENTS

EP    1037050    9/2000
EP    2098867    9/2009
(Continued)

OTHER PUBLICATIONS

English translation of Office Action in Chinese Patent Application No. 201280046063, dated Apr. 28, 2015, 13 pages.
(Continued)

*Primary Examiner* — Jamel E Williams
(74) *Attorney, Agent, or Firm* — Fish & Richardson P.C.

(57) ABSTRACT

Sample application systems can include an extraction mechanism to remove a sample from sample containers, a sample vessel disposed on a deployment mechanism, where the deployment mechanism is arranged to move the sample vessel to receive a sample, an extraction mechanism washing station to wash the extraction mechanism, a sample applicator to remove a portion of the sample in the sample vessel and apply it onto a sample carrier, where the deployment mechanism can move the sample vessel to a sample application position, a sample vessel washing station to wash the sample vessel, where the deployment mechanism can move the sample vessel to the sample vessel washing station, a sample applicator washing station to wash the sample applicator after the sample has been dispensed onto the sample carrier, and a fluid control system to control flow of a fluid provided to the extraction mechanism and the sample applicator.

26 Claims, 17 Drawing Sheets

Related U.S. Application Data division of application No. 13/548,773, filed on Jul. 13, 2012, now Pat. No. 9,057,672.

(60) Provisional application No. 61/510,700, filed on Jul. 22, 2011.

(51) Int. Cl.
*G01N 1/31* (2006.01)
*G01N 35/00* (2006.01)

(52) U.S. Cl.
CPC ......... *G01N 35/0099* (2013.01); *G01N 35/10* (2013.01); *G01N 35/1004* (2013.01)

(56) References Cited

U.S. PATENT DOCUMENTS

| | | | |
|---|---|---|---|
| 5,209,903 A | 5/1993 | Kanamori et al. | |
| 5,216,926 A | 6/1993 | Lipscomb | |
| 5,270,007 A | 12/1993 | Porte | |
| 5,314,825 A * | 5/1994 | Weyrauch | G01N 35/00663 356/246 |
| 5,501,984 A | 3/1996 | Hofstetter et al. | |
| 5,885,530 A | 3/1999 | Babson et al. | |
| 6,159,425 A | 12/2000 | Edwards et al. | |
| 6,171,280 B1 * | 1/2001 | Imazu | G01N 35/1079 604/118 |
| 6,318,158 B1 * | 11/2001 | Breen | B01F 11/0266 422/128 |
| 6,333,197 B1 * | 12/2001 | Le Comte | G01N 35/1065 436/52 |
| 6,544,799 B1 | 4/2003 | Lewis et al. | |
| 6,623,697 B2 | 9/2003 | Fuerst et al. | |
| 6,818,182 B2 | 11/2004 | Le Comte et al. | |
| 7,186,378 B2 | 3/2007 | Dunfee | |
| 7,578,853 B2 * | 8/2009 | Hattori | G01Q 30/20 250/306 |
| 7,579,190 B2 | 8/2009 | Ostgaard et al. | |
| 8,067,245 B2 | 11/2011 | van Ryper et al. | |
| 8,454,893 B2 * | 6/2013 | Helle | G05D 21/02 422/500 |
| 8,858,718 B2 | 10/2014 | Gifford et al. | |
| 9,057,672 B2 * | 6/2015 | McKeen | G01N 1/312 |
| 9,588,026 B2 | 3/2017 | McKeon et al. | |
| 2001/0004449 A1 | 6/2001 | Suzuki et al. | |
| 2003/0213313 A1 | 11/2003 | Katagi | |
| 2005/0074363 A1 * | 4/2005 | Dunfee | G01N 35/1004 422/81 |
| 2006/0024211 A1 * | 2/2006 | Giter | B01L 3/0231 422/404 |
| 2006/0105359 A1 | 5/2006 | Favuzzi et al. | |
| 2007/0041875 A1 * | 2/2007 | Bach | B01L 3/021 422/400 |
| 2007/0074363 A1 | 2/2007 | Bach | |
| 2009/0158862 A1 | 6/2009 | Londo et al. | |
| 2009/0275076 A1 * | 11/2009 | Knesel | G01N 1/2813 435/40.51 |
| 2009/0325299 A1 | 12/2009 | Hamada et al. | |
| 2009/0325309 A1 | 12/2009 | Favuzzi et al. | |
| 2010/0105074 A1 | 4/2010 | Covey et al. | |
| 2010/0284862 A1 | 11/2010 | Kakizaki et al. | |
| 2011/0189713 A1 * | 8/2011 | Le Comte | G01N 1/38 435/29 |
| 2012/0055269 A1 | 3/2012 | Londo et al. | |
| 2013/0021461 A1 * | 1/2013 | Zahniser | G01N 1/31 348/77 |
| 2014/0290706 A1 | 10/2014 | Ravalico et al. | |
| 2014/0302610 A1 | 10/2014 | Blouin et al. | |

FOREIGN PATENT DOCUMENTS

| | | | |
|---|---|---|---|
| EP | 2098868 | 9/2009 | |
| EP | 2098869 | 9/2009 | |
| EP | 2098870 | 9/2009 | |
| EP | 2098872 | 9/2009 | |
| EP | 2251696 | 11/2010 | |
| EP | 2251697 | 11/2010 | |
| FR | 2 196 714 | 3/1974 | |
| GB | 2034088 | 5/1980 | |
| GB | 2049179 | 12/1980 | |
| GB | 2075672 | 11/1981 | |
| JP | 52043487 | 4/1977 | |
| JP | H05-264561 | 10/1993 | |
| JP | H08-94506 | 4/1996 | |
| JP | H09-145718 | 6/1997 | |
| JP | 2011-137785 | 7/2011 | |
| WO | WO 93/12431 | 6/1993 | |
| WO | WO 97/11375 | 3/1997 | |
| WO | WO 9711375 A1 * | 3/1997 | ......... G01N 35/1004 |
| WO | WO 97/26541 | 7/1997 | |

OTHER PUBLICATIONS

English translation of Search Report in Chinese Patent Application No. 201280046063, dated Apr. 28, 2015, 4 pages.
English translation of Japanese Office Action dated Mar. 29, 2016 in corresponding JP Patent Application No. 2014-521671, 7 pages.
International Search Report and Written Opinion, dated Sep. 17, 2012, issued in international application No. PCT/US2012/046713, 11 pgs.
International Preliminary Report on Patentability, dated Feb. 6, 2014, in International Application No. PCT/US2012/046713, 7 pgs.
Examination report dated Mar. 7, 2014 in corresponding Australian application No. 2012287299, 4 pgs.
European Office Action in European Application No. 12746415.4, dated Feb. 7, 2017, 7 pages.

* cited by examiner

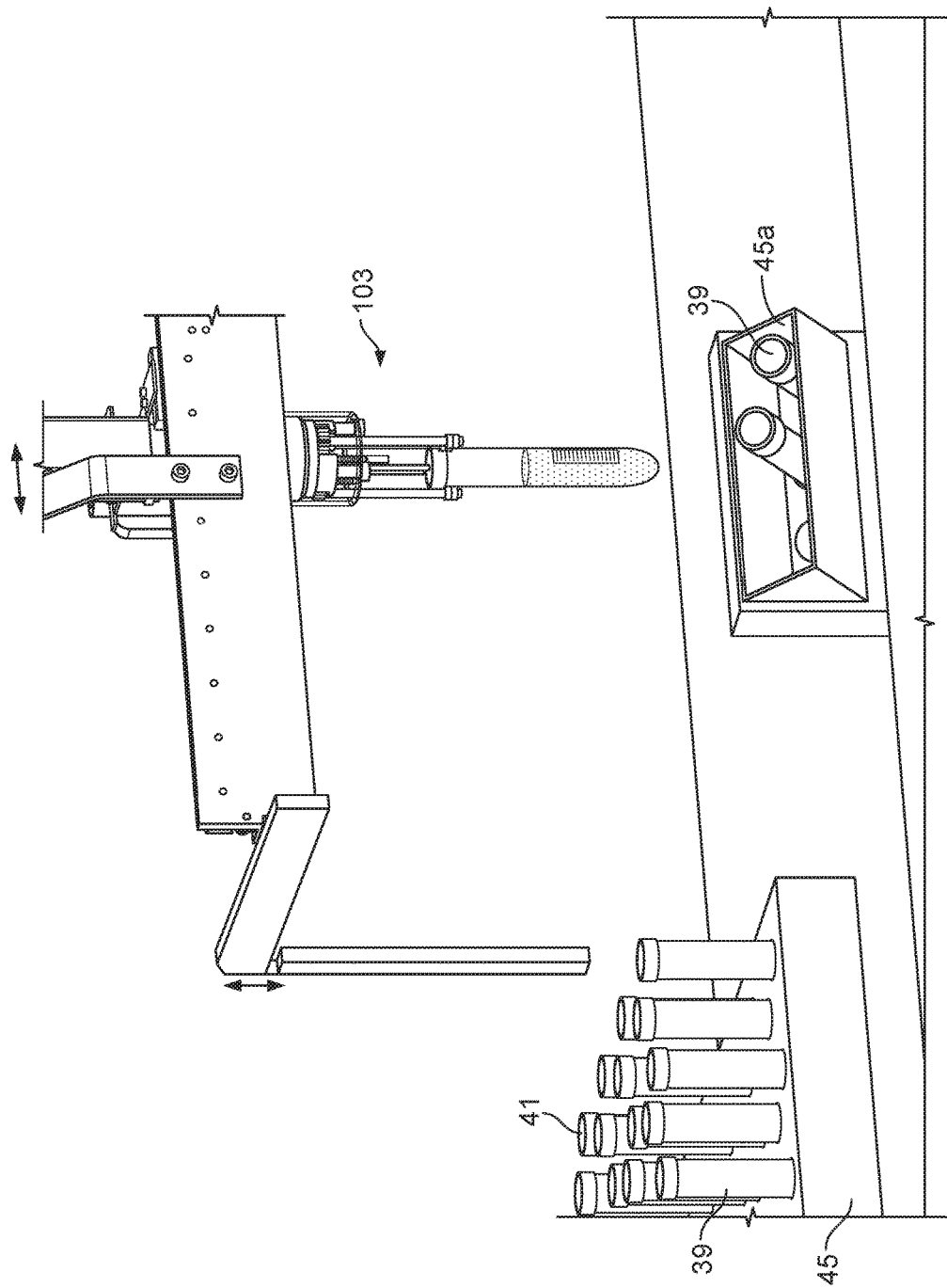

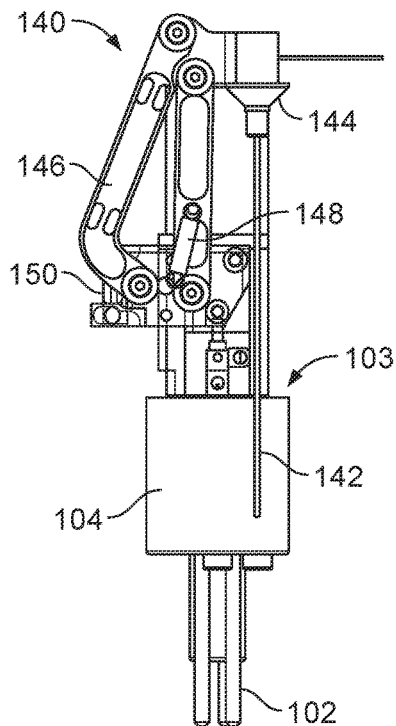
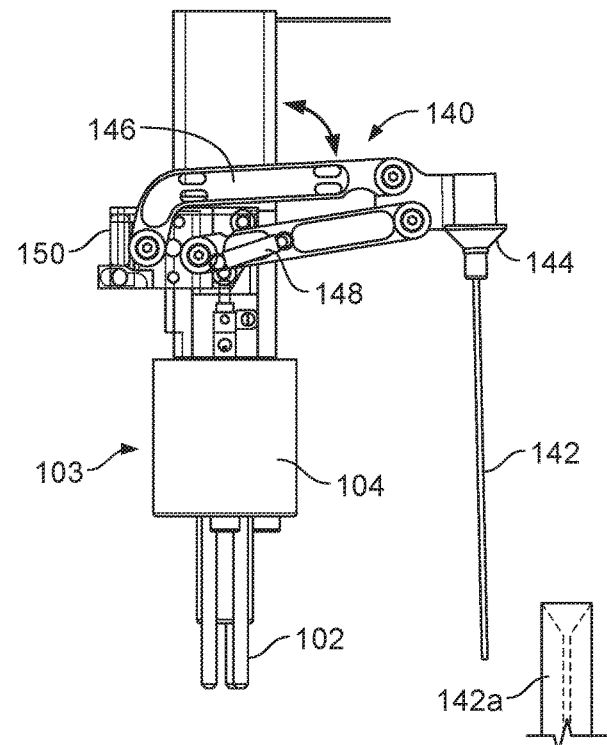
FIG. 5H    FIG. 5I
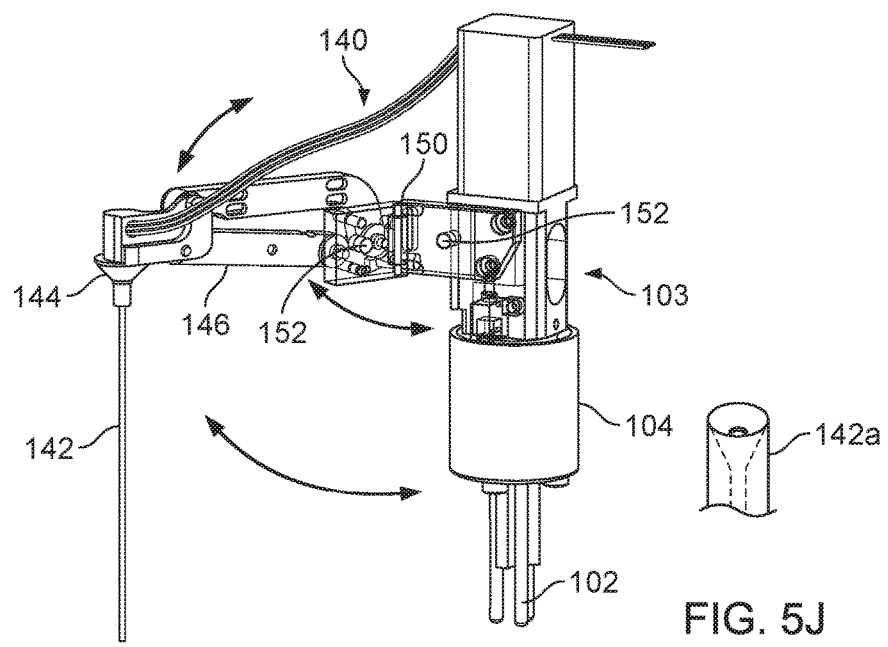
FIG. 5J

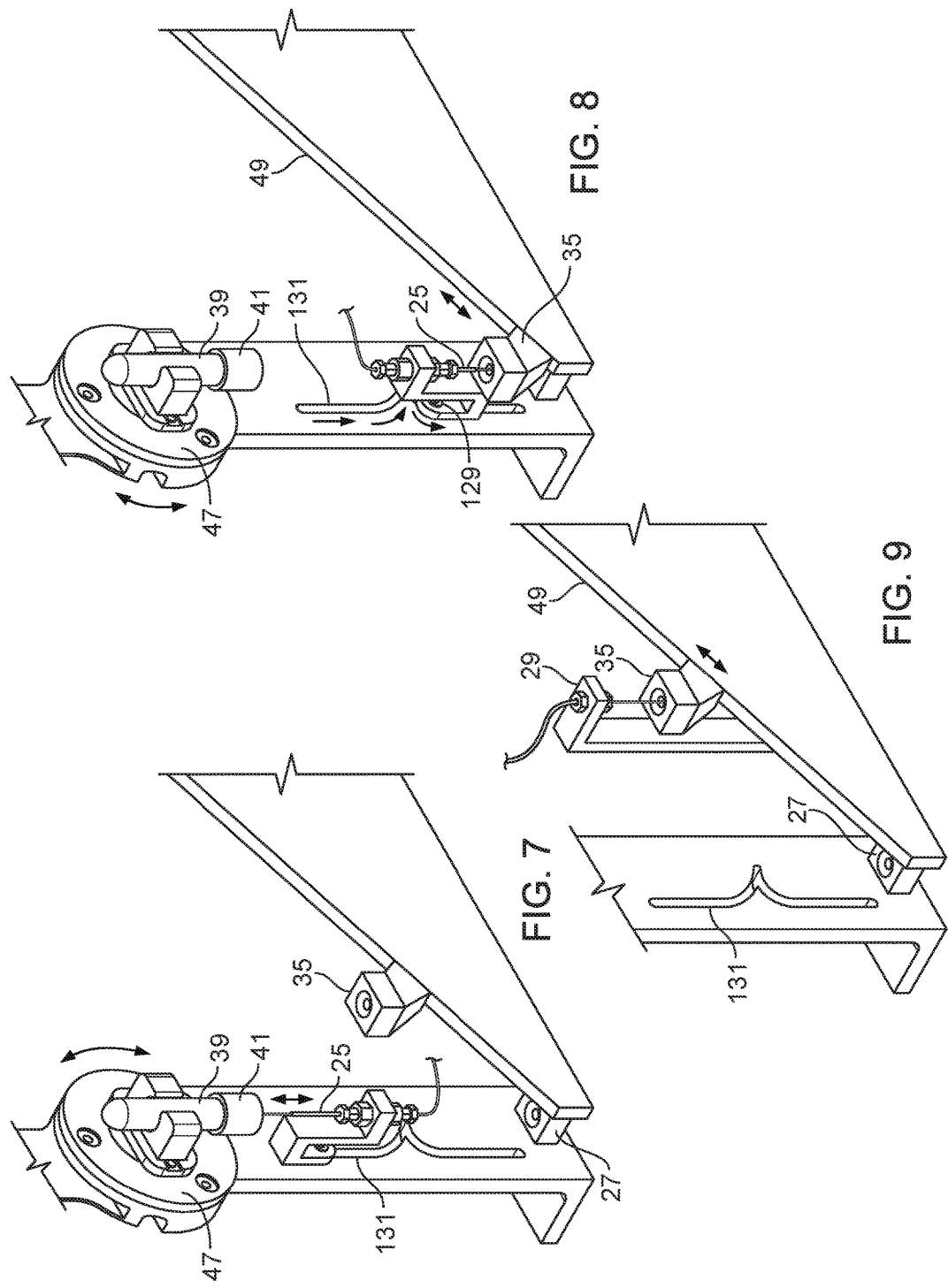

FLUID SAMPLE PREPARATION SYSTEMS AND METHODS

CROSS-REFERENCE TO RELATED APPLICATIONS

This application is a continuation application of, and claims priority to U.S. patent application Ser. No. 14/738,257, filed on Jun. 12, 2015, now U.S. Pat. No. 9,588,026, which is a divisional application of U.S. patent application Ser. No. 13/548,773, filed on Jul. 13, 2012, now U.S. Pat. No. 9,057,672, which claims priority to U.S. Provisional Patent Application No. 61/510,700, filed on Jul. 22, 2011, the entire contents of each of which are incorporated by reference herein.

TECHNICAL FIELD

This disclosure relates to the inspection of biological fluid samples, and more particularly to applying biological fluid samples to a surface, such as a sample carrier, e.g., a slide.

BACKGROUND

Systems, such as manufacturing systems or systems for analyzing samples, e.g., fluid samples, tissue samples, food samples, chemical samples, environmental samples, etc., can be used to analyze samples of different origins (e.g., body fluids from different patients or environmental samples from different regions). To permit automatic or semi-automatic operation of such systems (e.g., to minimize human interaction), electromechanical systems can be implemented to selectively provide samples to the systems for processing.

SUMMARY

Systems, such as manufacturing or testing systems, e.g., blood analysis systems, having multiple stations, e.g., processing, monitoring, or analysis stations, can be simplified by creating a sample preparation mechanism that can automatically or semi-automatically remove samples, e.g., fluid samples, tissue samples, food samples, chemical samples, or environmental samples, from sample containers and provide the samples to the manufacturing or testing systems while preventing cross-contamination of samples. In some implementations, the sample preparation mechanisms can operate via one or multiple fluid handling aspiration needles and a translating sample vessel that translates between a sample extraction position and a sample application position.

In one implementation, the present disclosure relates to sample application systems that include an extraction mechanism configured to remove a sample from a sample container (e.g., a test tube having a cap), a sample vessel disposed on a deployment mechanism, wherein the deployment mechanism is arranged to move the sample vessel into an extraction position in which the extraction mechanism can dispense a sample into the sample vessel, an extraction mechanism washing station arranged to wash the extraction mechanism after the extraction mechanism has dispensed the sample into the sample vessel, a sample applicator arranged to remove a portion of the sample in the sample vessel and apply the portion of the sample onto a sample carrier, wherein the deployment mechanism is arranged to move the sample vessel into a sample application position in which the sample applicator can remove the portion of the sample in the sample vessel, a sample vessel washing station arranged to wash the sample vessel after the sample applicator has removed the portion of the sample, wherein the deployment mechanism is arranged to move the sample vessel into a position in which the sample vessel washing station can wash the sample vessel, a sample applicator washing station arranged to wash the sample applicator after the sample applicator has dispensed the portion of the sample onto the sample carrier; and a fluid control system to control flow of a fluid provided to the extraction mechanism and the sample applicator.

Various implementations and embodiments of the sample application systems can include any one or more of the following features, individually or in combination. The extraction mechanism can include a conduit to penetrate a cap on a test tube. The deployment mechanism can include a leadscrew and sliding mechanism. The sample applicator can include a conduit to dispense the sample. The washing stations can each include a vessel having a rounded bottom to direct a fluid flow from a conduit inserted into the vessel to the outer surface of the conduit. The fluid control system can include a fluid reservoir, a fluid pump, and a controller to operate the fluid control system.

The sample application systems can further include an information reading device, wherein the sample container includes machine-readable information (e.g., a barcode or a radio-frequency identification tag). The sample application systems can further include a sample modification system, wherein the sample modification system can include a sample diluent system.

In another implementation, the present disclosure relates to methods of handling a sample. The methods include receiving a sample container containing a volume of a sample, removing a sample from the sample container using an extraction device, dispensing the sample into a sample vessel with the extraction device, washing the extraction device by dispensing a fluid through the extraction device, moving the sample vessel containing the sample to a sample application position, removing a portion of the sample from the sample vessel using a sample applicator, dispensing the sample portion from the sample applicator onto a sample carrier, rinsing the sample applicator by dispensing fluid through the sample applicator, and washing the sample vessel to remove any residual sample.

Implementations and embodiments of the methods described herein can include any one or more of the following features, individually or in combination. The extraction devices can be operated by a fluid system, wherein the fluid of the fluid system is separated from the sample by an air pocket within the extraction device. The methods can further include modifying the sample dispensed into the sample vessel, wherein modifying the sample can include adding a diluent fluid to the sample in the sample vessel. Removing a sample from the sample container can include inserting a needle through a cap attached to a test tube.

The extraction devices and the sample applicators can retain the sample when the fluid control system generates a vacuum in the extraction device and the sample applicator. Rinsing the extraction device and rinsing the sample applicator can include inserting a portion of the extraction device and a portion of the sample applicator into respective receptacles having curved bottoms, such that fluid dispensed from the extraction device and the sample applicator is directed along an outer surface of the extraction device and the sample applicator. Dispensing the sample portion from the sample applicator can include dispensing the sample portion onto a glass slide. The sample can include a body fluid (e.g., blood).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DESCRIPTION OF DRAWINGS

FIG. 5E is a perspective view of a test tube priority drawer.

FIG. 5H is a side view of an open mode port aspirator in a stowed position.

FIG. 5I is a side view of the open mode port aspirator of FIG. 5J in a deployed position.

FIG. 5J is a perspective view of the open mode port aspirator of FIG. 5J in a deployed position.

FIG. 7 is a perspective view of an extraction needle extracting a sample from a test tube.

FIG. 8 is a perspective view of the extraction needle of FIG. 7 rotating to provide the sample to a sample vessel.

FIG. 9 is a perspective view of the sample vessel of FIG. 8 translating to a diluent position under a diluent needle.

Like reference symbols in the various drawings indicate like elements.

DETAILED DESCRIPTION

For testing biological fluids and tissue, such as blood and other bodily fluids, the new systems and methods described herein can be used to receive the fluid (e.g., blood), specimen, or sample from a specimen container and apply it to a surface, such as a sample carrier, e.g., a glass or plastic slide, e.g., a microscope slide or cover slip, for processing and/or inspection at other locations or in other modules within a larger system (e.g., an analysis system).

Sample Preparation Systems

Figure 1:
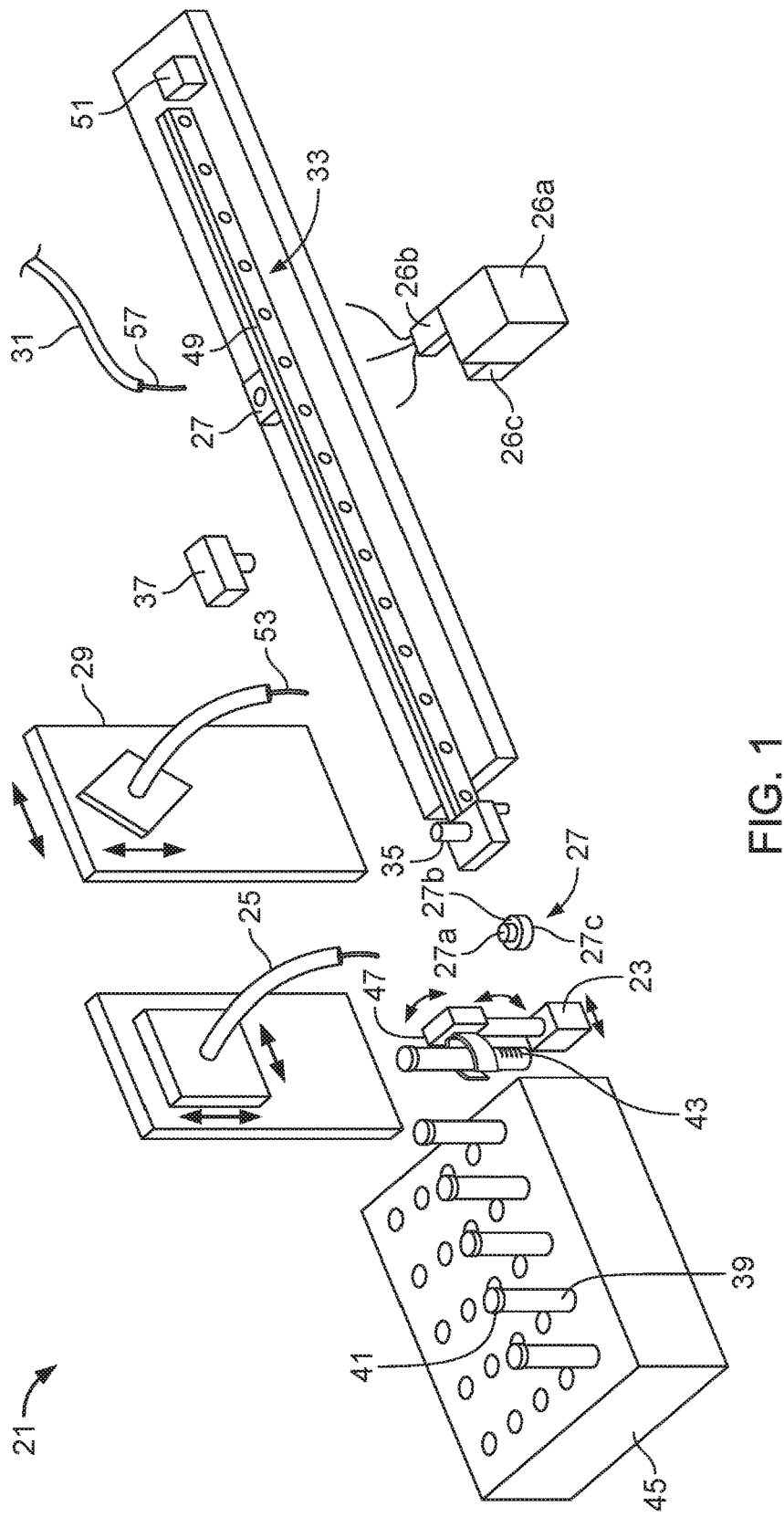
FIG. 1 is a perspective view of a sample preparation system.

FIG. 1 shows a sample preparation system 21 for preparing a fluid sample and applying the fluid sample to a surface such as a sample carrier, e.g., a slide. The sample preparation system 21 can include a sample container carrier 23, an extraction needle 25, a fluid reservoir 26a, a fluid pump 26b, a fluid system controller 26c, one or more wash cups 27, a modification system 29 such as a diluent system, a sample applicator 31, a sample vessel movement mechanism 33 to move a sample vessel 35 to the other components in the sample preparation system 21, and a sample vessel wash system 37.

One or more sample containers 39 can be provided to the sample preparation system 21 to contain and separate different samples, such as samples from different origins (e.g., body fluid samples from different patients or environmental samples from different locations). The sample containers 39 can include small cups or cylinders (e.g., test tubes). The sample containers 39 can be sealed to contain the sample when the sample is transported by the sample container carrier 23. In some implementations, sample containers 39 can include caps 41 (e.g., plug, stopper, cover, lid, or similar device, e.g., made of rubber, silicone, or plastic) to seal the sample containers.

The sample containers 39 can include sample information 43 regarding the sample contained therein. Sample information 43 can include things such as sample origin (e.g., name of patient that provided the sample or geographical location where the sample was obtained), type of sample (e.g., type of body fluid, type of environmental sample), time and date that the sample was obtained from its natural environment (e.g., when biological fluid was obtained from a body, when an environmental sample was removed from the environment). In some implementations, the sample information 43 can be in the form of a barcode or radio-frequency identification ("RFID") tag, or other machine-readable format, for simplified reading and processing by a control unit, e.g., with a barcode reader.

The sample containers 39 can be provided to the sample preparation system 21 in a sample container magazine 45. The sample container magazine 45 can be a device used to transport multiple sample containers 39 to and from the sample preparation system 21. The sample container magazine 45 has multiple openings or apertures to temporarily support the sample containers 39 such that the sample containers do not spill or lose the sample during transport (e.g., test tube sample containers are supported and held upright).

The sample container carrier 23 is used to remove sample containers 39 from the sample container magazine 45 so a sample aliquot or portion can be removed from the sample container 39. The sample container carrier 23 can operate in various ways to remove the sample container 39 from the sample container magazine 45. In some implementations, the sample container carrier 23 can be in the form of an articulating robotic device that can move to a location of a particular sample container 39 (e.g., where the particular sample container 39 is positioned in the sample container magazine 45), grip the particular sample container 39, and lift sample container 39 from the sample container magazine 45 high enough to clear other sample containers 39 held by and from protruding from the sample container magazine 45.

Alternatively, in other implementations, instead of having a robotic device that can move laterally to select a particular sample container 39 and also have the ability to lift the sample container 39 from the sample container magazine 45, the sample container carrier 23 can include a device to push sample containers 39 from the sample container magazine 45 by the bottom of the sample containers 39. Once the sample container 39 is pushed from sample container magazine 45 high enough to clear the other sample containers 39 held in the sample container magazine 45, a robotic device can grip the sample container 39 to remove it from the sample container magazine 45. After the sample container 39 is removed from the sample container magazine 45, it is transported to extraction needle 25.

In addition to transporting the sample container 39 from the sample container magazine 45, the sample container carrier 23 can also be used to prepare the sample for extraction. In some implementations, the sample container carrier 23 can include an inverting mechanism 47 such that the sample container 39 can be moved (e.g., rotated) to agitate the sample (e.g., re-suspend blood cells in a blood sample or to mix a non-homogeneous sample). For example, inverting mechanism 47 can rotate sample container 39 multiple times (e.g., 2, 3, 4, 5, or 10 or more) from an upright position to another position, e.g., to 90° or 180° from the upright position, so that the sample container is turned upside down, e.g., to re-suspend or mix a sample before aspiration. Inverting mechanism 47 can rotate sample containers through other degrees of inversion (e.g., 45°, 270°, or 360°). In some implementations, the inverting mechanism 47 rotates the sample container 180° so that the sample container is upside down (e.g., the cap 41 is pointed downward toward an extraction needle 25) to ensure that the extraction needle always contacts the sample within the sample container (rather than contacting air if the needle were inserted from the top into a container that is not completely filled with sample). After the sample has been removed, the sample container 39 is either returned to the magazine 45 (e.g., to the same location from which it was removed, or to a different, empty location in the magazine from which it was removed or a different magazine) or discarded.

Although the sample container carrier 23 has been described as a device used to remove a sample container 39 from a sample container magazine 45, in other implementations, sample containers 39 are not provided to the sample preparation system 21 using a sample container magazine 45. In such implementations a sample container 39 may be manually provided to the sample container carrier 23 by an operator.

The extraction needle 25 is a device that can be inserted to penetrate a cap 41 of the sample container 39 to extract a sample portion from the sample container 39. In some implementations, the extraction needle 25 and the cap 41 are designed such that after the extraction needle 25 is removed from the cap 41, the cap 41 automatically seals the hole made by the extraction needle 25, e.g., by an elastic or resilient nature of the material used to make cap 41. To remove fluid samples without cross-contaminating the extraction needle 25 or other samples, various material handling methods can be used. In some implementations, to extract and handle a fluid sample using the extraction needle 25, the extraction needle 25 is connected to a pneumatic or hydraulic system, e.g., a fluid system, such as a buffer fluid system, using tubing, e.g., to contain the fluid, e.g., buffer fluid. Buffer fluids for the fluid system that can be used to operate the extraction needle 25 and other components (e.g., sample applicator 21) can be contained in the fluid reservoir 26a and can be distributed to the components using the fluid pump 26b and the fluid system controller 26c. Motion of the buffer fluid (or simply air or other inert gas, such as nitrogen) within the tubing can be controlled by the fluid pump 26b to generate a vacuum or pressure to withdraw, control, and expel a fluid sample from the tip of the extraction needle 25.

The extraction needle 25 and the associated tubing have small inner diameters such that the gas or liquid, e.g., buffer fluid, contained therein can be suspended in the tubing without leaking. During operation of the system, the tubing, and in some cases a portion of the extraction needle 25, is filled with the buffer fluid that can be provided by the fluid reservoir 26a and fluid pump 26b. The remaining portion of the extraction needle 25 (e.g., the portion open to the surrounding environment not containing the buffer fluid) can contain an air gap so that when the buffer fluid in the extraction needle 25 or the connected buffer fluid tubing applies a vacuum within the extraction needle, the vacuum can be used to extract a sample fluid, such that the air gap remains between the fluid, e.g., buffer fluid, and the sample fluid, e.g. blood aspirated from a sample tube. Since the tubing and the amount of fluid contained in the tubing is relatively small, the air gap is not expected to dissolve or otherwise become entrapped in either the buffer fluid or the sample fluid.

In some implementations in which the sample container 39 is rotated 180° from the upright position (e.g., to invert the sample container 39) so that the sample fluid is extracted from the end of the sample container 39 that is facing downward (e.g., the end of the sample container 39 having the cap 41, facing downward), the extraction needle 25 can include a mechanism to rotate the extraction needle 25 as well as to articulate the extraction needle 25 upward, toward and through cap 41 and into the sample container 39 to extract the sample and downward, away from the sample container 39 to remove extraction needle 25 from the sample container 39. Articulation and rotation of the extraction needle 25 can be achieved by various devices such as electromechanical devices (e.g., servos, slide mechanisms, and/or electric motors) and/or mechanical devices (e.g., cams, gears, and/or leadscrews). In some implementations, the full range of motion of the extraction needle 25 (e.g., translating the extraction needle 25 into a sample container 39, removing the extraction needle 25 from the sample container 39, and rotating the extraction needle 25) can be achieved using just one motion input (e.g., one electric motor) in combination with other mechanical devices (e.g., one electric motor combined with a leadscrew and cam devices). In other implementations, multiple electromechanical devices can be used.

The wash cups 27 are devices used to clean various fluid aspirating and/or dispensing members (e.g., the extraction needle 25 and the sample applicator 31) after the members have handled a sample (e.g., after a sample has been extracted and dispensed).

In some implementations, the wash cups 27 utilize the same buffer fluid (e.g., a combined buffer and wash fluid composition, as further described below) contained in the fluid reservoir 26a and provided by the fluid pumps 26b used in the hydraulic vacuum system to clean the members (e.g., the extraction needle 25 and/or sample applicator 31). In such implementations, the wash cup 27 can have an inner basin 27a and an outer basin 27b with a fluid output device 27c (e.g., a drain or suction device), and operate by dispensing a portion of the buffer fluid from the member such that the buffer fluid flushes any sample remnants from the inner surface of the member. The inner basin 27a can be designed such that it directs the buffer fluid exiting the member to flow along the outer surface of the needle before flowing into the outer basin 27b to drain away from the wash cup 27. By directing the buffer fluid in one continuous flow path (e.g., out of the needle, then along the outer surface of the needle, and then to the outer basin 27b and drain), the possibility of backflow of a buffer fluid contaminated with a sample is reduced. In such implementations, after buffer fluid has been dispensed into the wash cup 27 and the member is removed from the wash cup 27, the buffer fluid system can withdraw remaining buffer fluid back into the member and connected tubing to create an air pocket or gap so that the member can properly handle the next sample.

In other implementations, a wash cup 27 can be in the form of the cup or vessel having a nozzle to provide a wash fluid solution and/or drying nozzles to remove any residual cleaning solution from the needles or conduits.

The sample vessel 35 is a vessel, such as a cup used to contain and carry a fluid sample portion to multiple locations during sample preparation. In some implementations, the sample vessel 35 can serve as a mixing vessel when the fluid sample portion is modified (e.g., diluted, buffered, or stained). Since the sample vessel 35 will typically contain a large number of different samples, such as samples from different origins (e.g., blood from different patients) or different types of samples (e.g., different types of body fluids) it should be formed from a material that is smooth and non-porous to prevent absorption of the sample into the material. The material should also be chosen such that the sample vessel 35 will be inert and tend to repel liquid (e.g., reduce wetting) so that sample fluids will collect at the bottom of the sample vessel 35 more easily for removal from the sample vessel 35. Such materials can include various types of plastics (e.g., Teflon®, Delrin®, or Noryl®), glasses, or some metal materials, and in some cases the sample vessel material can be polished to increase the sample vessel's ability to repel residue fluids.

In some implementations, the sample preparation system 21 can include a sample vessel wash system 37 to clean the sample vessel 35 and to remove any residual fluid sample remnants. The sample vessel wash system 37 can include a nozzle to provide a wash fluid to the sample vessel 35 and a suction head to remove the rinse fluid containing any residual fluid sample.

Alternatively, in some implementations, the sample vessel 35 can include an outlet (e.g., a drain) built into the sample vessel 35 so that residual fluid samples, or wash fluid is removed from the sample vessel 35 using the drain system.

The sample vessel movement mechanism 33 is a device to move the sample vessel 35 to the various components in the sample preparation system 21 to allow for automated or semi-automated treatment of samples (e.g., minimize human interaction) during sample preparation. In some implementations, the sample vessel movement mechanism 33 can include a track 49 on which the sample vessel 35 moves (e.g., slides) and a translating mechanism 51 (e.g., an electric motor connected to a leadscrew or an actuator) to move the sample vessel 35 to the various components (e.g., the extraction needle 25, the modification system 29, and/or the sample applicator 31) positioned along the track 49 such that the sample vessel 35 can stop at several locations along the track 49. In some implementations, the track 49 and translating mechanism 51 can be one component having a track 49 and a translating device (e.g., a pneumatic linear actuator, an electromechanical linear actuator, or an indexing table) used to move the sample vessel 35 along the track 49. Alternatively, in some implementations, the sample vessel 35 can remain stationary and the various components can move (e.g., the modification system 29 and the sample applicator 31 could be mounted to an indexing table that rotates to modify and withdraw a fluid held in a stationary sample vessel 35).

The modification system 29 can include various systems to prepare a sample for use in an analysis system such as a diluent system, a staining system, and/or an anti-coagulation system. Generally, the modification system 29 includes a device to provide a modifying substance (e.g., a metered amount of diluent such as saline, purified water, or protein solutions) to the sample contained in the sample vessel 35. In some implementations, the modification device can include a modification conduit 53 (e.g., a syringe or a pipette) connected to a fluid reservoir to provide the modifying substance (e.g., diluent).

The sample applicator 31 is a device used to remove a sample (e.g., a sample prepared with a modifying substance or an unmodified sample) from the sample vessel 35 and provide the sample to a surface, such as a sample carrier (e.g., a glass slide) of an analysis system (e.g., body fluid analysis system). The sample applicator 31 can include an application conduit 57 (e.g., a portion of tubing, a needle, a syringe tip, and/or a pipette) to withdraw and handle a fluid sample. The sample applicator 31 can also include a buffer fluid system connected to the application conduit 57, similar to the extraction needle 25, so that the sample applicator 31 can use fluid pumps to withdraw a sample from the sample vessel 35 and dispense the sample onto the sample carrier. To reach a sample vessel 35, the sample carrier of the analysis system, and a wash cup 27, the sample applicator 31 can include a sample applicator translating device 32 to move the sample applicator 31 in different directions to the various positions (e.g., multiple axes of motion).

Buffer and Wash Fluid Compositions

Buffer and wash fluids, e.g., combined buffer and wash fluid compositions, can be used with the sample preparations systems described herein. A combined buffer and wash solution can be used to operate the extraction needle 25 and sample applicator 21, as well as to clean and flush a sample preparation system. As a wash solution, the compositions can reduce cross-contamination between biological specimens. In some embodiments, the buffer and wash solution can have reduced or no precipitation and can be stable over a period of time (e.g., more than two weeks, more than one month, more than 6 months, more than one year, more than 1.5 years, or more than two years). Generally, the buffer and wash solution can be an aqueous solution. The solvent can include distilled water or deionized water. The solution can include a buffering agent. Examples of buffering agents include HEPES buffer (e.g., HEPES sodium salt and/or HEPES free acid), bis-tris buffer, phosphate, MES, Tris, and organic buffers having a pH between 5 and 8. The buffer and wash solution can include from approximately 0.5 mM (e.g., 25 mM, 50 mM, 100 mM, 150 mM, or 200 mM) to approximately 250 mM (e.g., 200 mM, 150 mM, 100 mM, 50 mM, or 25 mM) of a buffering agent. For example, the solution can include approximately 1.0 mM HEPES, which can decrease the likelihood of pH change due to formation of carbonic acid in an aqueous solution.

The buffer and wash solution can include one or more antimicrobial agents to inhibit the growth of microorganisms and increase the shelf life of the solution. The antimicrobial agents can be or include benzalkonium chloride, 5-chloro-2-methyl-4-isothiazolin-3-one, 2-methyl-4-isothiazolin-3-one, such as ProClin® (e.g., ProClin 300®), polyamino carboxylic acids (e.g., ethylenediaminetetraacetic acid, disodium ethylenediaminetetraacetic acid, and calcium disodium ethylenediaminetetraacetic acid), azides, thimerosols, merthiolates, and/or antibiotics. In some embodiments, the antimicrobial agent includes 5-chloro-2-methyl-4-isothiazolin-3-one and 2-methyl-4-isothiazolin-3-one. For example, the antimicrobial agent can be ProClin 300®, available from Sigma-Aldrich. The antimicrobial agent can be present at a concentration of approximately one part in 1,000 to one part in 10,000 (e.g., one part in 2,000, one part in 4,000, one part in 6,000, or one part in 8,000). In some embodiments, the buffer and wash solution contains approximately 100 ppm benzalkonium chloride or ProClin 300®.

In some embodiments, the buffer and wash solution can include a surfactant. The surfactant may be non-ionic, cationic, anionic or zwitterionic. Mixtures of surfactants may also be used. Exemplary classes of surfactants include alcohol ether sulfates, alcohol sulfates, alkanolamides, alkyl sulfonates, amine oxides, amphoteric surfactants, anionic surfactants, betaine derivatives, cationic surfactants, disulfonates, dodecylbenzene, sulfonic acid, ethoxylated alcohols, ethoxylated alkyl phenols, ethoxylated fatty acids, glycerol esters hydrotropes, lauryl sulfates, mono and diglycerides, non-ionic surfactants, phosphate esters, quaternary surfactants, and sorbitan derivatives. Additional examples of surfactants suitable for embodiments of the buffer and wash solution are disclosed in co-pending U.S. patent application Ser. No. 13/526,164 filed on Jun. 18, 2012, the disclosure of which is incorporated herein by reference in its entirety.

In some embodiments, the buffer and wash solution further includes an acid to adjust the pH. The acid can be any acid traditionally used to adjust the pH of a solution. For example, acetic acid, nitric acid, hydrochloric acid, phosphoric acid, formic acid, sulfuric acid, or citric acid can be used. If necessary, a base can be added as well to reduce the pH to the desired level.

The buffer and wash solution can have a pH of from approximately 5 to approximately 9 (e.g., from approximately 5.5 to 8.5, from approximately 5.5 to 8, from approximately 5.5 to 7, from approximately 5.5 to 6, from approximately 5.8 to 7.2, from approximately 6.8 to 7.2, a pH of approximately 6.0, a pH of approximately 6.5, or a pH of approximately 7).

One way to make the buffer and wash solution, is to add distilled or deionized water to a mixing vessel to less than 100% (e.g., approximately 90%) of the final desired volume. Calculated amounts of an antimicrobial agent (e.g., ProClin 300®), an acid (e.g., acetic acid), and a buffering agent (e.g., HEPES) can then be added to the water. Further water can be added to bring the solution to its final desired volume. The mixture can be mixed with a magnetic stir plate/stir bar and/or an impeller for a minimum of about 30 minutes. Other ways to prepare the solution can be used. After mixing, a pH reading can be carried out on an aliquot of the wash solution using a pH meter (e.g., a Mettler pH meter). In some embodiments, if the pH is not within a desired range, then further acid can be added to the wash solution until the desired pH is attained.

Finally, the buffer and wash solution can be filtered through a 0.45 μm filter to remove any particulates before bottling. In some embodiments, a finer filter can be used. For example, a 0.1 to one μm filter (e.g., a 0.2 μm filter, a 0.4 μm filter, a 0.8 μm filter) can be used to remove any microorganisms and/or particulates in the wash solution. In some embodiments, the buffer and wash solution can be stored in a five-liter bottle. The pH of the final product can be measured, if desired.

Systems for Analyzing Samples

Figure 2:
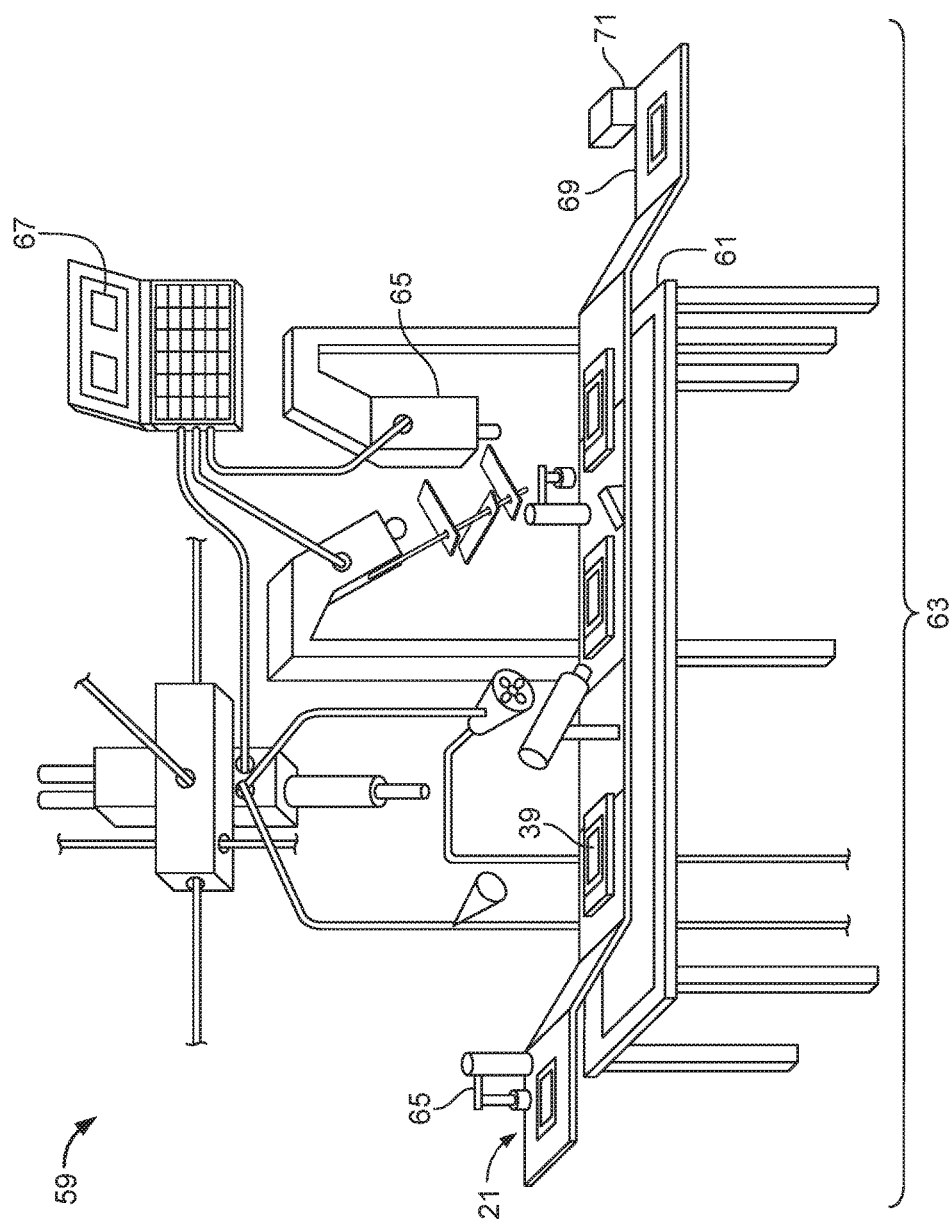
FIG. 2 is a perspective view of an analysis system for analyzing samples such as fluids, e.g., body fluids.

FIG. 2 shows an analysis system 59 for analyzing samples such as body fluids. As discussed in U.S. Patent Application Nos. US2009/0269799 and US2011/0070606, and in U.S. patent application Ser. No. 12/943,687, systems for analyzing fluid samples can include subsystems and components to inspect body fluids such as blood, cerebrospinal fluid, and lymph, or other fluids, e.g., that contain cells. Components can include a chassis 61, a sample preparation system 21, a sample carrier transport system 63, one or more processing stations 65, a slide output station 69, a sample carrier labeler 71, and a control unit 67.

The chassis 61 can support the components of the analysis system 59. In some implementations, the chassis 61 is in the form of a platform or a table onto which system components are secured.

The analysis system 59 can include one or more processing stations 65 to perform various processes. When analyzing a biological fluid, processing stations 65 can include a sample applicator, a sample preparation station, and/or one or more imaging stations. Additionally, the analysis system 59 can contain stations that do not have processing components to possibly reserve the location for future needs or uses. Processing stations 65 can be positioned in a straight direction with respect to one another, or alternatively the processing stations 65 can be positioned in an arc or other shapes based on system and/or space requirements.

To transport the samples to each of the stations of the analysis system 59, a sample carrier transport system 63 can have a translating member having two or more carrier retaining devices attached used to move the sample carriers 55 to each of the processing stations 65.

Although the analysis system 59 shown in FIG. 2 has one sample carrier transport system 63, in some implementations, the analysis system 59 can include two or more sample carrier transport systems 63. For example an analysis system 59 can include two or more sample carrier transport systems 63 working in parallel.

Systems and methods for analyzing body fluids are disclosed, for example, in U.S. Patent Application Publication Nos. 2011/0070606 and 2012/0149050, the entire contents of each of which are incorporated herein by reference. As one example, sample preparation system 21 can be used to deliver a sample to a sample carrier. In some implementations, for analysis systems that analyze fluid samples such as body fluids (e.g., blood, bone marrow, urine, semen, bile, breast milk, cerebrospinal fluid, lymph, gastric fluid, mucus, peritoneal fluid, sweat, tears, and/or saliva), one or more fluid samples can be provided to the analysis system 59 in one or more sample containers 39 (e.g., test tubes) arranged in sample container magazines (e.g., test tube racks). In such implementations, the sample preparation system can be configured to remove a small amount of the fluid sample from a sample container 39 (e.g., a test tube) and apply the sample to a sample carrier (e.g., a glass slide) using the sample applicator. Such sample applicators can be powered hydraulically or pneumatically using suction to withdraw the fluid sample from the sample container 39 and then using pressure to dispense the fluid into or onto the sample carrier. The sample preparation system can further include systems to clean any sample handling devices to minimize cross-contamination of samples.

Depending on the type of samples analyzed by the analysis system 59, other types of sample applicators are possible. For example, if tissue samples are analyzed, the sample applicator could include a mechanical device to pick up the tissue, such as tweezers or forceps, and deposit the tissue sample evenly across the surface of a sample carrier.

Some sample types such as body fluids (e.g., blood, bone marrow, urine, semen, bile, breast milk, cerebrospinal fluid, gastric fluid, mucus, peritoneal fluid, lymph, sweat, tears, vomit, and/or saliva) can be analyzed with a stain applied to permit certain types of visual inspection. In such analysis systems, a sample preparation station can be provided to apply one or more fixative, stain, and/or rinse solutions to the sample carried by the sample carrier.

To inspect or analyze the sample using the imaging station, a light source is generally included in the analysis system to illuminate the sample. Depending on the type of analysis to be conducted, the light source can include various types of visible light sources (e.g., light emitting diodes, incandescent lights, fluorescent lights, and/or lasers) or non-visible light source (e.g., ultraviolet light and infrared light sources). The positioning of the light source relative to the imaging station can depend on the type of analysis conducted, as well as on the type of sample carriers used. In some implementations, where samples are carried on glass slides, an LED light source can be positioned below the glass slides to illuminate the sample.

The imaging station is electrically connected to the control unit 67 and can be used to collect data from samples (e.g., can take an image of the sample to perform algorithms or analyses using the image). In some implementations, the imaging station can use the image to perform analyses such as counting blood cells in a sample or to detect specific cells in the blood. As discussed above, in some implementations, the light source can provide different forms of light so the imaging station can therefore include other types of detectors such as infrared light detectors or laser detectors used to measure certain properties (e.g., dimensions) of the sample.

Once the analysis system has processed the sample at all of the processing stations 65, the slide output station 69 can disposition the sample, either discarding the sample or retaining the sample for additional processing or future evaluation.

In such cases where it is desired to retain the sample and/or sample carrier for additional processing or inspection, the sample carrier labeler 71 (e.g., a printer device) can be used to provide sample information to the sample and/or to the sample carrier. For analysis systems that analyze a patient's body fluids, the patient's information can be printed onto the sample carrier.

The control unit 67 can be electrically connected to the various components of the analysis system to control the operations of the components, such as controlling the sample preparation system 21, sample carrier transport system 63, the light source, the imaging system, and the sample carrier labeler 71.

Providing a Sample to a Sample Applicator

Figure 3:
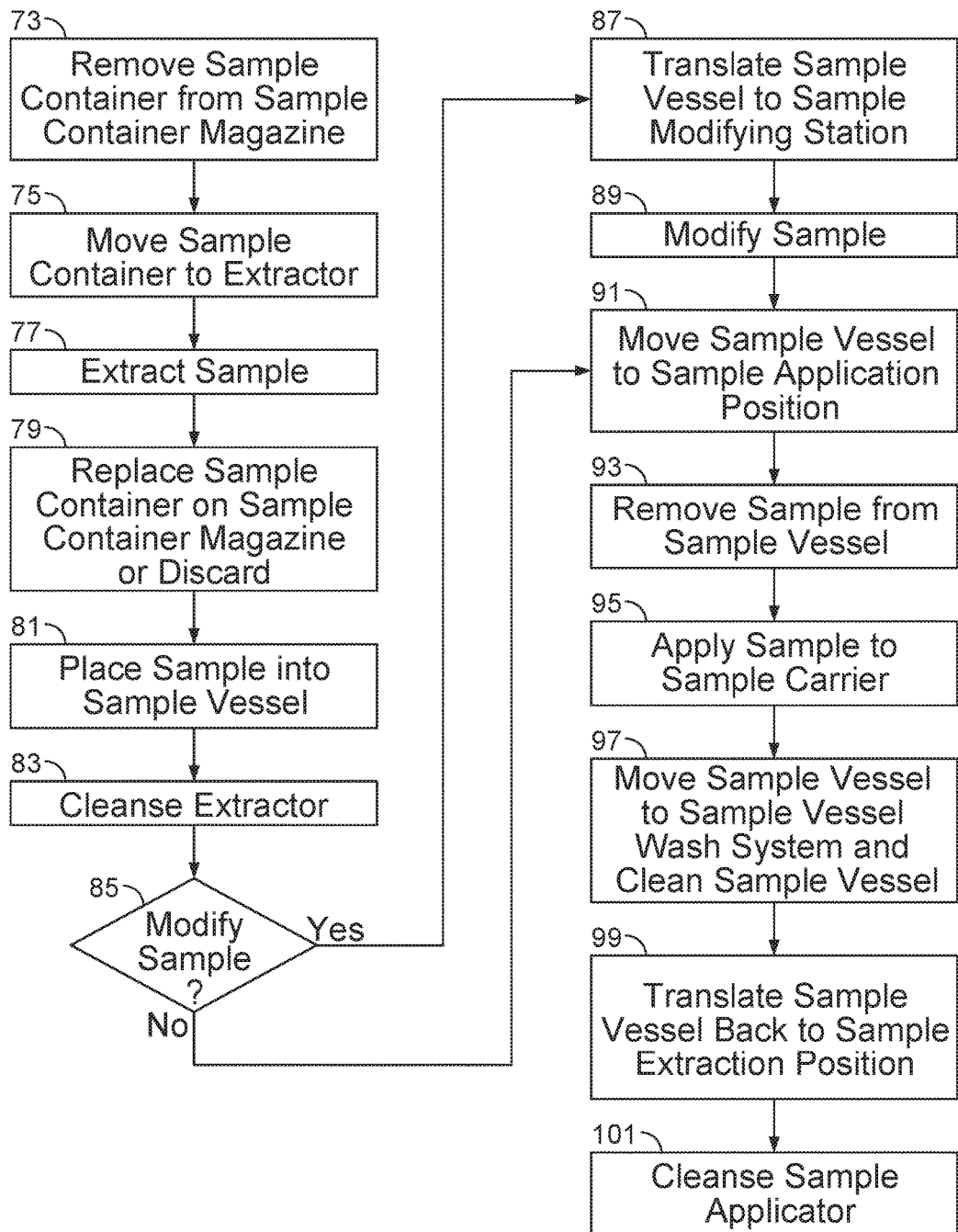
FIG. 3 is a flow chart of one embodiment of a sample preparation system.

FIG. 3 shows a flow chart describing an embodiment of a method and sequence of removing a sample from a sample container (e.g., a test tube) and providing the sample to a sample applicator system of a sample analysis system (e.g., a blood analysis system).

In this example, the sample preparation system includes one or more sample containers (e.g., test tubes) supported by a sample container magazine (e.g., test tube rack), a sample container carrier, an extraction device (e.g., an extraction needle), a sample vessel to contain and transport the sample through the sample preparation system, a wash cup for the extraction device, a modifying station, a sample applicator, a sample applicator wash cup, and a sample vessel wash system to clean the sample vessel after the fluid sample has been provided to the sample applicator.

As shown in FIG. 3, to begin processing a first sample, a sample container (e.g., a test tube) is removed from the sample container magazine (step 73) (e.g., test tube rack) by a sample container carrier. As discussed above, the sample container carrier can include a robotic device (e.g., a robotic arm) that can articulate to grab or pick up the sample container and remove it from the sample container magazine.

The sample container carrier then places the sample container in position for sample extraction (step 75) and a sample is extracted from the sample container (step 77). In some implementations, this includes translating the sample container to be in line with an extractor needle and rotating the sample container such that it is positioned above the extractor needle, with a sample container cap (e.g., penetrable cap) pointed downward towards the extractor needle. In such implementations, the extractor needle is inserted through the sample container cap, which can be made of a rubber or plastic material, and into the sample container far enough to penetrate through the cap to remove a liquid sample. When the sample is extracted with the sample carrier upside down, it can be more likely that a sample will be successfully extracted from the sample carrier, then when a sample is extracted with the sample container positioned upright. When a sample is extracted with the sample container positioned upright, a certain volume of fluid is typically required in the sample container to ensure that the extraction needle can reach the fluid surface level during extraction. However, in other implementations, the sample can be extracted while the sample container is in the upright position using methods to verify that a sample is properly extracted.

Using either method of handling the sample containers and extracting a sample, once the sample is extracted from the sample container, the sample container carrier can place the sample carrier back in the sample container magazine (step 79). In some cases, the sample containers are placed into the same position in the sample container magazine from which they were removed prior to extraction of the sample. In other cases, the sample container can be placed in a different position within the sample container magazine, or alternatively the sample container can be placed into a different sample container magazine than the sample container magazine from which it was removed.

With the sample removed from the sample container, the sample can be placed into a sample vessel using the extractor needle (step 81). As discussed above, in some implementations, the extractor needle can operate to handle the sample by using a hydraulic fluid, e.g., a buffer fluid, system to withdraw the sample and suspend it in the needle while the needle is in motion. In such implementations, the buffer fluid is controlled to move within the tubing and/or extractor needle just enough to dispense the suspended sample into the sample vessel without dispensing the buffer fluid.

Once the sample is dispensed into the sample vessel, the sample vessel can be moved away from the position where it receives the sample (e.g., the sample extraction position) using a movement mechanism such as a track (e.g., a pneumatic powered track, or a translating track and lead-screw device).

Once the sample vessel travels away from the sample extraction position, the extraction needle can be cleaned (step 83). As discussed above, in some implementations, the extraction needle can be inserted into a wash cup and a portion of the buffer fluid can be expelled from the needle to wash the inner surface and then the outer surface of the extraction needle.

In some implementations, the sample vessel can be moved to a modification station prior to the sample being withdrawn from the sample vessel by a sample applicator (step 87). In such implementations, a modifying station can be positioned at a location along the track between the extractor needle and the sample applicator. In some cases, the sample modification can include adding a diluent fluid to the sample. In such cases, a modification conduit (e.g., a fluid nozzle, a needle, a syringe tip, a pipette tip, and/or a tubing portion) connected to a modifying fluid reservoir is positioned along the track such that the sample vessel can stop under the modification conduit and a portion of the modifying fluid (e.g., diluent fluid) can be applied to the sample in the sample vessel (step 89).

Where the modification station includes preparing a sample using a diluent, diluents may include salt solutions or protein solutions. Salt solutions range from "physiological saline" (0.9 N), to complex mixtures of salts, to the commercial preparation Plasmalyte that simulates virtually all the salts found in human blood serum. Protein solutions can range from simple solutions of bovine albumin to Plasmanate®, a commercial preparation with selected human plasma proteins. Such preparations can vary in protein concentrations, buffers, pH, osmolarity, osmalality, buffering capacity, and additives of various types. Synthetic or "substitute" versions of these solutions may also be usable, including Ficoll® or Dextran or other polysaccharides. Other substitutes may be used. An example of a diluent is Plasmalyte plus Plasmanate® in the proportion of 4:1 (Plasmalyte:Plasmanate®). Another example of a diluent is 5% albumin. When preparing samples from whole blood, a dilution of 2 parts blood to 1 part diluent can be used, where the diluent is a physiologically compatible solution, but a range of dilution from 0:1 (no dilution) to 10:1 (diluent:blood) can be used in alternate embodiments.

In some implementations, the sample is not subjected to any modification prior to being provided to the sample application, and thus the sample vessel and sample can be moved along the track from the sample extraction position directly to the applicator position (step 91).

Once the sample vessel and sample is moved to the sample applicator, the sample applicator can withdraw the sample from the sample vessel (step 93). The sample applicator can include an application conduit (e.g., a fluid nozzle, a needle, and/or a tubing portion) connected to a pneumatic or hydraulic fluid, e.g., buffer fluid, system, similar to the pneumatic or hydraulic system used with the extractor needle. To remove the sample from the sample vessel, vacuum can be applied to the hydraulic, e.g., buffer, fluid to generate low pressure in the tip of the application conduit. Such pressure can withdraw the sample into the application conduit such that an air gap between the buffer fluid and the withdrawn sample fluid is generated. In some cases, it can be advantageous to remove the entire fluid sample from the sample vessel.

After all or a portion of the sample is removed from the sample vessel, the sample vessel can be removed from the applicator position. In some cases, after the sample has been removed, the sample vessel is translated away from the sample applicator back toward the sample extraction position (e.g., at the extraction needle). In other cases, the track can extend beyond the location of the sample applicator, so the sample vessel can move beyond the applicator position before returning back to the sample extraction position.

With the sample vessel no longer in the sample application position, the sample applicator can apply the sample to a surface such as a sample carrier (step 95) (e.g., a cup, a flat plate, or a glass slide) so that the sample can be processed in another system (e.g., analyzed in an analysis system). In some implementations, the sample applicator can be connected to an articulating device that allows the sample applicator to move to apply the sample to the surface. Typically, during application of a sample, the sample applicator dispenses substantially the entire sample contained in the sample applicator. Depending on the type of sample and the requirements of the system in which the sample will be used, various application patterns (e.g., a boustrophedon pattern, a raster pattern, a continuous spiral pattern, a pattern of multiple concentric circles, and/or a pattern of multiple parallel lines) can be applied to the application surface. Alternatively or additionally, the sample applicator can remain stationary and the sample carrier surface can be moved relative to the sample applicator to apply the appropriate pattern of sample.

In some cases, the sample applicator does not dispense all of the fluid sample volume when applying the sample. In such cases, some portion of the fluid sample can be retained in the sample applicator and/or a residual amount of the fluid sample can accumulate on the outer surface or edge of the application conduit of the sample applicator. To avoid any cross contamination of samples, the application conduit of the sample applicator can be cleaned after applying the sample (step 101). Similar to the extractor needle, the application conduit of the sample applicator can be cleaned by inserting a distal portion of the application conduit into a wash cup and expelling a portion of the hydraulic, e.g., buffer fluid out of the application conduit into the wash cup that is shaped having a curved bottom to direct the flow exiting the application conduit up and over the outer surface of the application conduit to wash any fluid sample portion from both the inside surface and the outside surface of the application conduit.

Prior to returning to the sample extraction position, the sample vessel can be moved to a sample vessel wash system to clean the sample vessel (step 97). In some implementations, as discussed above, the sample vessel wash system can include a nozzle to dispense a cleaning fluid to flush residual sample fluid from the sample vessel. The sample vessel wash system can also include a vacuum device to remove the cleaning fluid from the sample vessel, leaving the mix up cleaned. In other implementations, the sample vessel can include a drain device to dispose of the cleaning fluid provided to the sample vessel.

Once the sample vessel is cleaned, it can be moved along the track and returned to the sample extraction position (e.g., under the extractor needle) to receive a next sample obtained from a sample container (step 99). In some implementations, the next sample can be obtained from a next sample container. However, alternatively, in other implementations, multiple sample aliquots (e.g., 2, 3, 4, 5, 10, or more sample aliquots) can be removed from the same sample container.

Although FIG. 3 shows one example of the sample preparation system utilizing certain steps performed in a certain order to provide a sample to a sample applicator, in other embodiments, the sample preparation system can include more or fewer steps, or some of the steps can be performed in different orders. For example, although FIG. 3 shows step 101 (cleanse sample applicator) as being the last step in the process, in other embodiments, the sample applicator can be cleaned before some of the other steps, e.g., before step 99 (translate sample vessel back to sample extraction position).

Example of a Sample Preparation System

Figure 4:
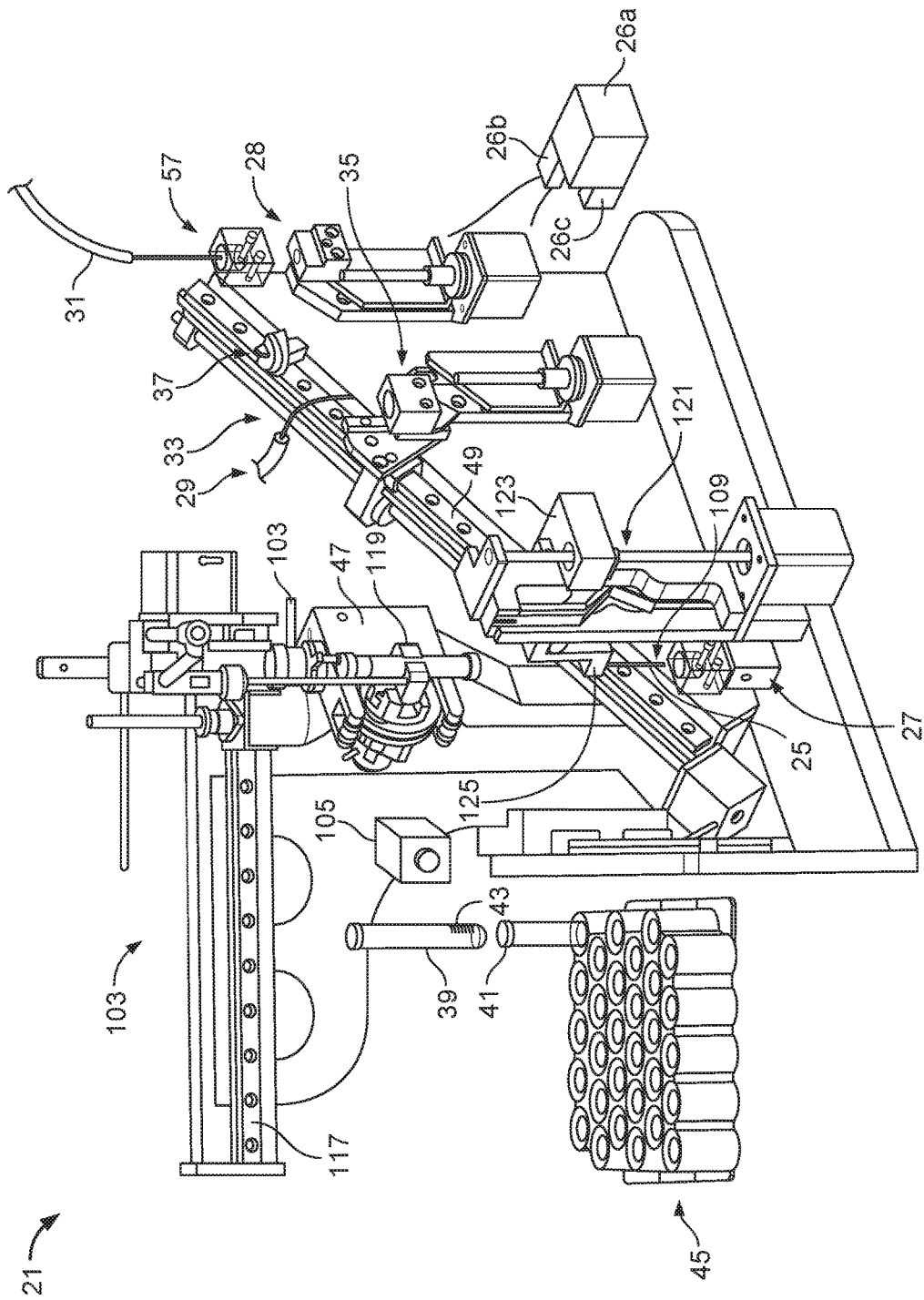
FIG. 4 is a perspective view of an example of a sample preparation system.

FIG. 4 shows an example of a sample preparation system 21 used in a biological fluid analysis system. The sample preparation system 21 removes a fluid sample such as a body fluid (e.g., blood, bone marrow, urine, semen, bile, breast milk, cerebrospinal fluid, gastric fluid, mucus, peritoneal fluid, sweat, tears, and/or saliva) from sample containers 39 (e.g., test tubes), and provides the sample to a sample applicator 31 of the biological fluid analysis system. The sample preparation system 21 can include a sample container gripping device 103, an information reading device 105 (e.g., a barcode reader), an inverting mechanism 47, a fluid extraction device 109, a sample vessel 35, a sample vessel movement mechanism 33, a sample vessel wash system 37, a sample modification system 29 (e.g., a diluent system), a sample applicator 31, an extraction needle wash cup 27, a sample applicator wash cup 28, a fluid reservoir 26a, a fluid pump 26b, and a fluid system controller 26c.

One or more sample containers 39 used in the sample preparation system 21 can be in the form of test tubes having container closures 41 (e.g., test tube caps) to contain the samples when the test tubes are moved or agitated. The test tube caps are typically made of a plastic material or a rubber material so that they can have the ability to re-seal punctures created by a needle (e.g., extraction needle 25). The test tubes are generally provided to the sample preparation system 21 in a sample container magazine 45 (e.g., a test tube rack) for simplified storage and transport of multiple sample containers 39.

In some implementations, the sample containers 39 are test tubes and the test tubes can have sample information 43 (e.g., machine-readable information such as a barcode) printed onto their outside surface. In some cases, sample information 43 can include the type of sample, the origin of the sample, the time and/or date when the sample was obtained.

The gripping device 103 can be used to remove a test tube 39 from the test tube rack 45. As shown, in some implementations, the gripping device 103 can include two, three, or more finger members 102 that use radial motion to articulate inward and outward to temporarily retain a test tube 39. In some cases the finger members can move inward to grip the test tube 39 by a bottom lip of the test tube cap 41 such that the gripping device 103 provides a lifting force to the test tube cap 41 instead of a clamping force to the test tube 39, which could potentially damage the test tube 39.

Such a gripping device 103 also allows for retrieving a particular test tube 39 in a limited space envelope, without disturbing surrounding test tubes 39 that may be present. In some cases, radial motion used to articulate the finger members inward and outward can be achieved by a gear system, a cam system, or by electromechanical systems.

In other implementations, other mechanisms could be used to grip the test tube 39 and remove it from the test tube rack 45. For example, other mechanical systems or magnetic systems can be used. In such magnetic systems, the test tube 39 and/or test tube caps 41 could include magnetic portions and the gripping device 103 could include an electromagnetic device that could be activated to magnetically fasten to the test tube 39 and/or test tube cap 41 and pick it up.

Figure 5A:
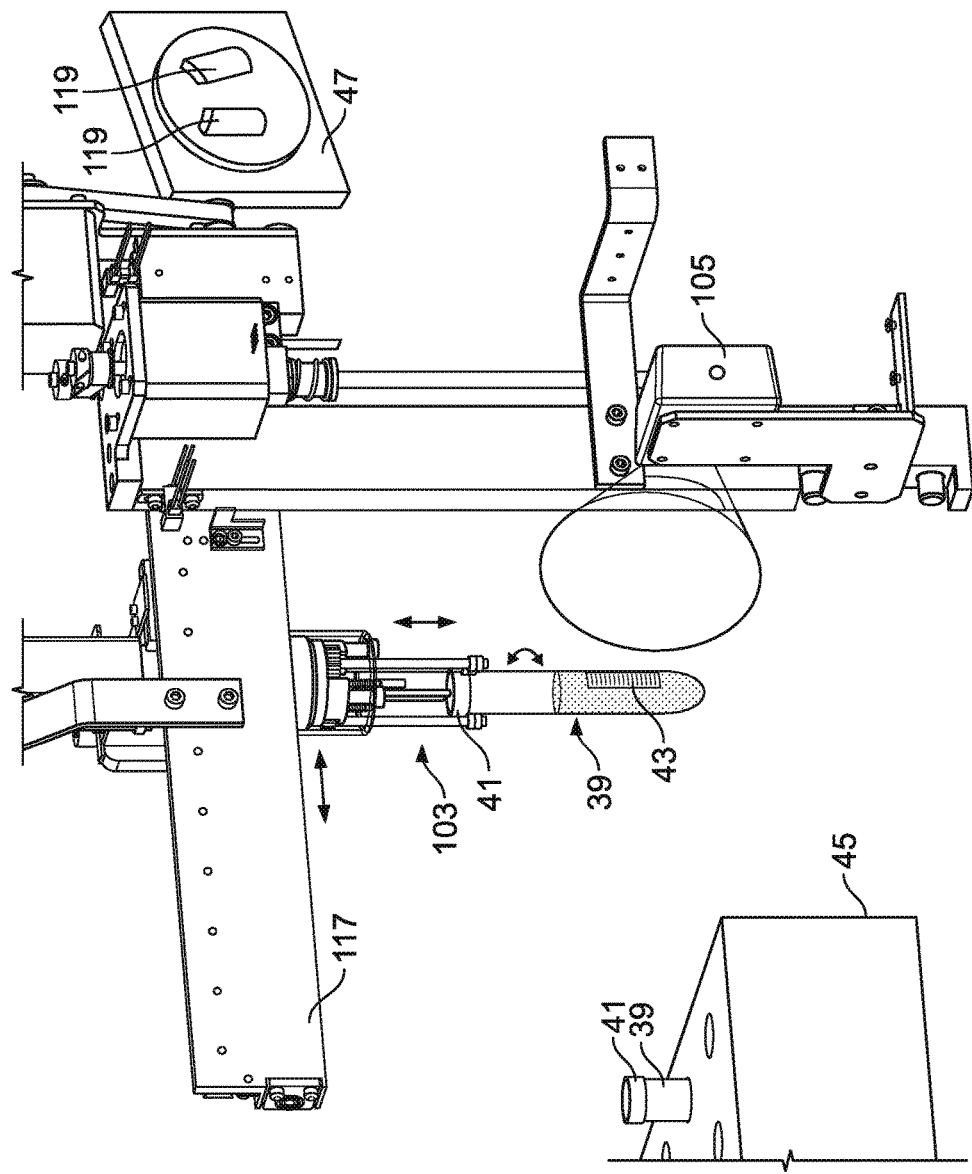
FIG. 5A is a perspective view of a tube gripping device transporting a test tube to an inverting mechanism.

As shown in FIG. 5A, in some implementations, the gripping device 103 can remove the test tube 39 from the test tube rack 45 and also rotate the test tube 39 about its longitudinal axis using electromagnetic and/or mechanicals systems (e.g., electric motors, servos, gears, and/or cams) to pass the test tube 39 by an information reading device 105, such as a barcode reader. As discussed above and shown in FIG. 5A, in some implementations, the test tube 39 can have sample information 43 (e.g., in the form of a barcode) printed on the outer surface of the test tube 39, so as the test tube 39 is rotated in front of the barcode reader 105, the barcode reader 105 can read the barcode 43 to obtain information regarding the sample. In other implementations, the barcode reader 105 can be mounted on an articulating member so that the barcode reader 105 can move around a test tube 39 to read the barcode.

Alternatively, in some implementations, barcodes or other machine-readable information can be applied to the test tube 39 at certain locations relative to a point of reference on the test tube 39 (e.g., at a certain angle with respect to the position of the test tube 39) such that as the test tube is removed from the test tube rack 45, the gripping device 103 can be programmed to rotate the test tube 39 so that a certain portion of the test tube 39 (e.g., the portion containing the barcode) is in a position in front of the barcode reader 105.

In some implementations, the gripping device 103 can be mounted on a translating track 117 (e.g., a linear actuator or an xyz robot) to move the gripping device 103 from the test tube rack 45 where it can pick up a test tube 39, move the test tube 39 in front of the barcode reader 105, and then provide the test tube 39 to the inverting mechanism 47.

Figure 5B:
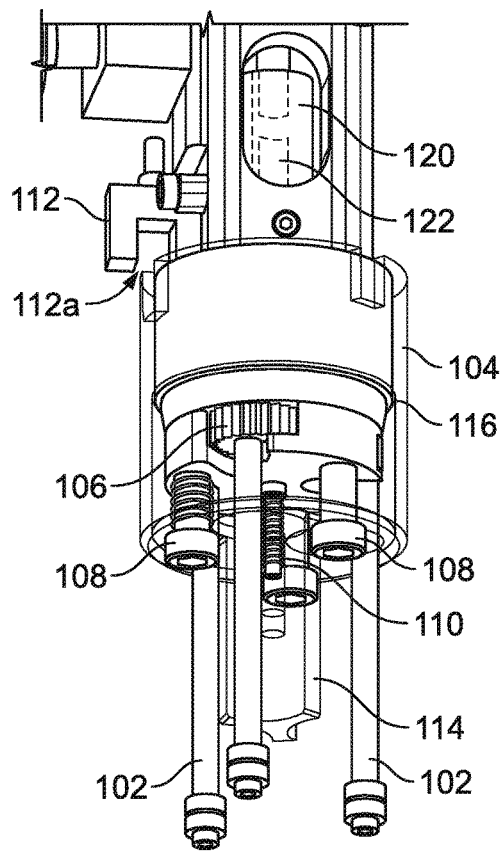
FIG. 5B is a perspective view of a cap detection device of a tube gripping device.

FIG. 5B shows a gripping device 103 having a cap detector cover 104 (shown in FIG. 5B to be semi-transparent to show the interior components) that is used to detect a test tube 39 and/or a test tube cap 41 positioned on a test tube 39 in a test tube rack 45. The cap detector cover 104 partially encloses multiple pinion gears 106 that rotate to move two or more finger members 102 inward and outward radially to grip and release a test tube 39. The cap detector cover 104 is typically free to translate in the longitudinal direction and is prevented from rotating about its longitudinal axis relative to the pinion gears 106 by one or more rotation limiting devices 108 (e.g., shoulder screws) that can also act as bottom stops to provide a lower resting position for the cap detector cover 104. Typically, the force of gravity and the weight of the cap detector cover 104 are sufficient to cause the cap detector cover 104 to rest at its lowest position along the shoulder screws 108. In some implementations, a deflection device 110 such as a spring or weight can be included to provide additional force to cause the cap detector cover 104 to be at rest at its lowest point.

As shown in FIG. 5B, a sensor 112, such as an optical sensor (e.g., an optical isolator sensor) can be positioned above the cap detector cover 104 so that when the gripping device 103 is lowered to a test tube 39, an elongated boss 114 of the cap detector cover 104 can contact the top of the test tube cap 41. Since the cap detector cover 104 is able to move relative to the gripping device 103, when the cap detector cover 104 is prevented from moving downward due to the presence of the test tube 39 or test tube cap 41, the rest of the gripping device 103 continues to move downward and therefore the cap detector cover 104 moves upward relative to the gripping device 103. The cap detector cover 104 can continue to move upward relative to the rest of the gripping device 103 until the sensor 112 is tripped (e.g., when an outer portion of the cap detector cover 104 passes into a slot 112a of the optical isolator sensor 112 shown in FIG. 5B) and causes the gripping device 103 to stop moving downward.

The sample preparation system 21 can use this method of articulating downward and detecting the position where the cap detector cover 104 contacts a test tube 39 or a test tube cap 41 to determine whether a test tube 39 is present in the test tube rack 45, the size of the test tube 39 present in the test tube rack 45, and whether or not a test tube 39 has a test tube cap 41 affixed on top by electronically storing and accessing known ranges (e.g., positions) at which the gripping device 103 should expect to contact a test tube 39 or a test tube cap 41.

For example, for sample preparation systems 21 that are configured to remove samples from test tubes 39 that are 75 mm or 100 mm long, if a test tube 39 is present in the test tube rack 45, the cap detector cover 104 should make contact with the top of a test tube cap 41 and trip the sensor 112 at one of at least two positions (i.e., positions associated with where a test tube cap 41 affixed to the top of a test tube 39 should be) located at distances from the bottom of a test tube rack, the distances corresponding to a test tube height (e.g., 75 mm or 100 mm) plus the height of a test tube cap. If the cap detector cover 104 fails to trip the sensor 112 at either of these predicted two positions, the sample preparation system 21 can be alerted that a test tube 39 is not present in the intended test tube rack location.

In addition to detecting if a test tube 39 is present in the test tube rack 45, the gripping device 103 can also utilize the motion of the cap detector cover 104 to determine whether or not a test tube cap 41 has been inadvertently omitted from, or has fallen off of, a test tube 39 present in the test tube rack 45. Similar to storing predicted positions where the sample preparation system 21 should expect the cap detector cover 104 to contact the top of a test tube cap 41 affixed on a test tube 39, indicating that a test tube 39 having a test tube cap 41 is properly positioned in the test tube rack 45, the system can also store positions (e.g., in a computer control system) where the cap detector cover 104 could contact the top of a test tube 39 that does not have a test tube cap 41 affixed thereon, indicating that a test tube 39 is positioned in the test tube rack 45, however the test tube 39 would not have a test tube cap 41. Therefore during operation when the gripping device 103 translates downward to remove a test tube 39 from the test tube rack 45, the gripping device 103 can monitor the travel distance of the gripping device 103.

As the gripping device 103 moves downward, the sample preparation system 21 can expect the sensor 112 to be tripped at a position that would indicate contact with a test tube cap 41 affixed onto the largest test tube (e.g., 100 mm test tube having a test tube cap). If the sensor 112 is not tripped at that position, the gripping device 103 continues to move downward and the sample preparation system 21 can expect the sensor to be tripped at a position that would indicate contact with the top of the largest test tube (e.g., 100 mm test tube) that does not have a test tube cap. If tripped at this position, it would indicate that a test tube 39 is positioned in the test tube rack 45, but that it does not have a test tube cap 41 disposed thereon and the sample preparation system 21 should not remove and/or process that particular test tube. If this occurs, the sample preparation system 21 conveys an error message to an operator and/or logs the occurrence in an error log or equivalent record.

If the cap detector cover 104 fails to trip the sensor 112 at either of these positions associated with the top surface of a test tube cap 41 positioned on a large test tube 39, or the top surface of the large test tube 39 itself, the gripping device 103 can continue to translate downward to detect a smaller test tube (e.g., a 75 mm test tube). Similar to having predicted positions to detect a large test tube, the sample preparation system 21 can have predicted positions where it expects the cap detector cover 104 to contact the top surface of a test tube cap 41 positioned on the smaller test tube 39, or the top surface of the smaller test tube itself 39. Similar to the large test tube 39, if the cap detector cover 104 does not contact the top surface of a test tube cap 41 affixed on a small test tube 39, the gripping device 103 will continue to translate to determine if a small test tube 39 is positioned in the test tube rack 45 without a test tube cap 41. If the sample preparation system 21 detects a small test tube 39 positioned in the test tube rack 45 without a test tube cap 41 disposed thereon, the sample preparation system 21 can be directed to not remove that particular test tube 39 for processing.

If the cap detector cover 104 fails to trip the sensor 112 at any of the expected positions, the sample preparation system 21 can determine that no test tube 39 is present in that particular test tube rack position and the sample preparation system 21 can alert an operator of the error, or alternatively log the error in an internal system, and move on to a next test tube 39 to be processed. Alternatively or additionally, in some implementations, a camera system can be used to verify proper placement of test tubes 39 within a test tube rack 45 during removal of the test tube 39 from the test tube rack 45 or during replacement of a test tube 39 to a test tube rack 45.

Figure 5C:
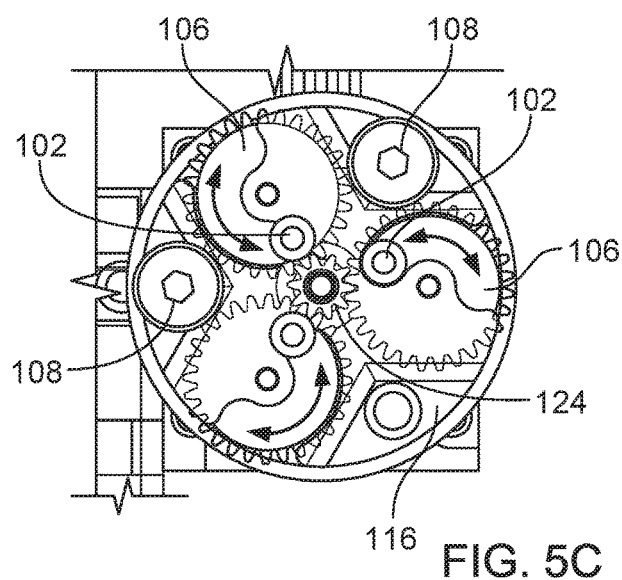
FIG. 5C is a bottom view of a gear system of the tube gripping device of FIG. 5B.

Once the sample preparation system 21 determines that the gripping device 103 is properly positioned above a test tube 39 having a test tube cap 41 to be processed, the finger members 102 can move inward radially to grip the test tube 39 by the test tube cap 41. As shown in FIGS. 5B and 5C, the gripping device 103 includes a cam device 106, such as a set of planetary gears, with each finger member 102 affixed at an off-center position on each gear 106. The planetary gears 106 can be mounted on a gripping device rotating frame 116. In the illustrated example shown in the cross-sectional view of FIG. 5D, the gear drive rotating assembly can include a motor 118 having a shaft that is connected to a gear drive rotating assembly including a coupling 120, pinion shaft 122 having a central gear 124 attached to its lower end, and a clutch mechanism 126 (e.g., a friction clutch) connected to the pinion shaft 122 and the rotating frame 116.

Figure 5D:
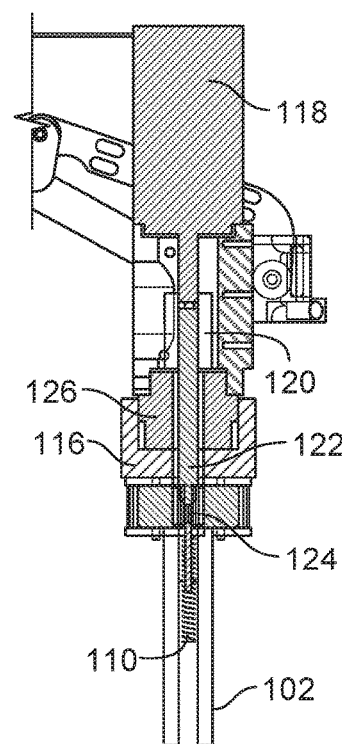
FIG. 5D is a cross sectional view of a rotating assembly of the tube gripping device of FIG. 5A.

As the shaft of the motor 118 rotates, the gear drive rotating assembly can also rotate. As the central gear 124 rotates due to the motor rotation, the outer planetary gears 106 rotate accordingly (shown in detail in FIG. 5C). As the planetary gears 106 rotate, the finger members 102 that are mounted at off-center positions along the planetary gears 106 move inward or outward radially. With the finger members 102 moving inward radially, the motor 118 can continue to rotate until the finger members 102 contact a test tube and cannot move further inward. FIG. 5D shows a cross-sectional view of the gripping device rotating assembly.

As shown in FIG. 5D, the pinion shaft 122 that is connected to the central gear 124 is also connected to the friction clutch 126 such that when a sufficient resistive force is applied to the rotation of the central gear 124 with respect to the planet gears 106, the friction clutch 126 is engaged and the entire rotating frame 116 rotates about its central axis. Therefore, when the finger members 102 move inward radially and contact a test tube 39, the friction clutch 126 engages and the rotating assembly and test tube 39 begin rotating about their longitudinal axis (shown in FIG. 5A). As discussed in detail above, this rotational motion of the test tube 39 can be used to rotate the test tube 39 in front of a machine to read information contained on the outer surface of the test tube (e.g., a barcode reader 105). Similar to the way the rotating frame 116 can rotate when the finger members 102 are moved inward and reach a mechanical stop (e.g., the test tube), the friction clutch 126 can also cause the rotating frame 116 to rotate in the opposite direction when the finger members 102 have reached their most outward radial positions (e.g., after a test tube is released) and the finger members come into contact with the rotating frame 116. Rotating the gripping device 103 in such a manner after it releases a test tube 39 can be performed in cases where it is desired for the finger members 102 to be positioned in a certain orientation when the gripping device 103 is translated downward to grip a test tube 39 (e.g., in cases where the test tubes can be packaged tightly together).

In addition to the benefits described above, generating the inward and outward radial motion of the finger members 102 using the rotating gears 106 allows for on-the-fly adjustments of the sample preparation system 21 and gripping device 103 so that different types of test tubes 39, such as test tubes having different diameters (e.g., 13 mm and 16 mm) or even sample carriers having different outer shapes (e.g., circular, square, triangular, or other shapes) can be removed from test tube racks 45 without using multiple gripping devices 103.

Although the test tubes 39 have been described as being provided while disposed in a test tube rack 45, in some implementations, the sample preparation system 21 can alternatively or additionally obtain a sample from a test tube 39 that is positioned in an accelerated response receptacle, such as a priority drawer or rack 45a (as shown in FIG. 5E). The priority drawer or rack 45a can include one or more apertures configured to receive a test tube 39. During operation of the sample preparation system 21, an operator may have a sample that he/she wishes to prepare for inspection before the other samples disposed in test tubes 39 position in the test tube racks 45. The priority drawer 45a provides a location in which an operator can place such high priority samples contained in test tubes 39 to undergo accelerated preparation and analysis by the system.

Accordingly, the sample preparation system 21 can be configured such that when an operator places a test tube 39 in one of the apertures in the priority drawer 45a, the sample preparation system 21 can process the test tubes 39 in the priority drawer 45a before processing the other test tubes 39 in the test tube rack 45. If more than one test tube 39 is present in the priority drawer 45a, the sample preparation system 21 can process all of the test tubes 39 present in the priority drawer 45a before continuing on to process samples contained in test tubes 39 in the test tube rack 45. When processing samples contained in test tubes 39 positioned in the priority drawer 45a, the griping device 103 can typically be operated in the same manner discussed above with respect to removing test tubes 39 from a test tube rack 45.

As shown in FIGS. 5A, 5F, 5G, and FIGS. 6-8, the inverting mechanism 47 can be a device including two or more closure members 119 (e.g., clamping jaws) that can clamp a test tube 39 to rotate the test tube 39 about an axis which is perpendicular to the longitudinal axis of the test tube 39 (e.g., to turn the test tube 39 upside down). In some implementations, the clamping jaws 119 can utilize electromechanical devices such as an electric motor and leadscrews or servos to open and close the clamping jaws 119. An electric motor can be used to rotate the inverting mechanism 47.

In some implementations, depending on the type of sample contained in the test tube 39, it can be beneficial to agitate the sample contained in the test tube 39 (e.g., blood can be agitated to re-suspend the blood cells or to mix non-homogenous samples). In such implementations, the inverting mechanism 47 can be used to fully invert test tube 39 multiple times (e.g., 10 times) to achieve a desired level of agitation. In other implementations, the inverting mechanism 47 can be used to partially rotate the test tube 39 without fully inverting it (e.g., rocking the test tube 30°-70° one or more times) to achieve a desired level of agitation. Once the sample is ready for sample extraction (e.g., once the sample has been agitated, if required), the test tube 39 can be rotated such that the test tube cap 41 is pointed downward so a sample portion can be extracted.

Referring back to FIG. 4, the fluid extraction device 109 is a device used to remove a sample from the test tube 39 and can include an extraction needle 25 and an extraction needle rotating mechanism 121 positioned under the inverting mechanism 47. In some implementations, as discussed above, the test tube 39 can include a test tube cap 41, which the extraction needle 25 can penetrate. In such implementations, the extraction needle 25 can be fluidly connected to a hydraulic, e.g., buffer, fluid system connected to the fluid reservoir 26a and the fluid pumps 26b. Using the fluid pumps 26b, the fluid system can generate movement and pressure changes within the buffer fluid to apply suction and withdraw the sample into the extraction needle 25.

In some implementations, the test tube 39 is rotated into an inverted position (e.g., the test tube cap 41 is pointed downward); therefore the extraction needle 25 is inserted upward into the test tube 39 to extract a sample. By extracting the sample from the test tube 39 while the test tube 39 is inverted, the extraction needle 25 typically only needs to puncture and barely penetrate the test tube cap 41 to contact the sample. If the test tube 39 was upright and the extraction needle 25 was inserted from the top, a minimum sample volume and height in the test tube 39 would typically be required to ensure that the extraction needle 25 would be in contact with the sample when inserted.

Figure 5F:
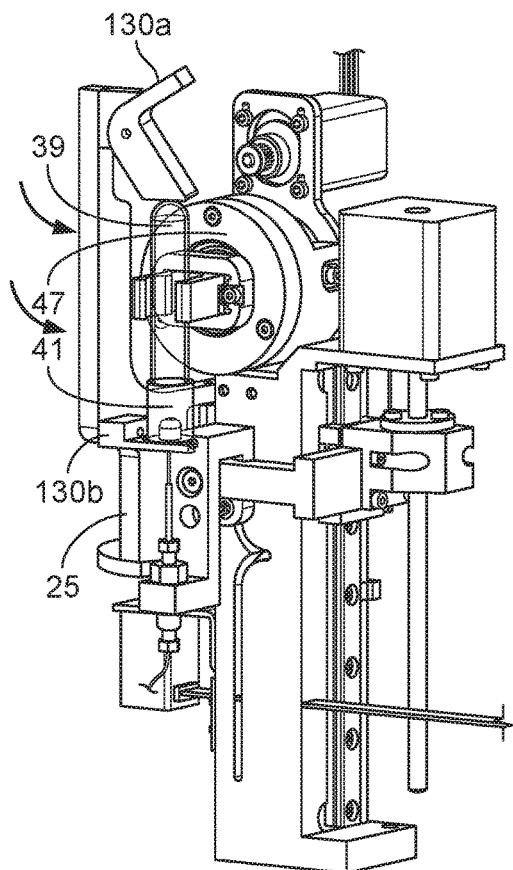
FIG. 5F is a perspective view of a test tube stop securing a small test tube.

In some implementations, a sample preparation system 21 can include a test tube stop 130 to temporarily secure the test tube 39 in the vertical direction so that when an extraction needle 25 is inserted into and/or removed from the test tube cap 41, the test tube 39 remains in a desired position to help ensure that the extraction needle 25 can properly penetrate into and be removed from a test tube cap 41. As shown in FIG. 5F, the test tube stop 130 can be mounted on a hinge assembly 132 to move away from the test tube path as the test tube 39 is moved towards the inverting mechanism 47 and when the test tube 39 is gripped and rotated by the inverting mechanism 47, the test tube stop 130 can rotate (e.g., using a ring gear and a pinion gear attached to an electric motor) around the hinge 132 to secure the test tube 39.

The test tube stop 130 can include a rotating portion 130a and a fixed portion 130b. The rotating portion 130a is provided to prevent the test tube 39 from moving upward (e.g., when the extraction needle 25 is inserted into the test tube cap 41) and can be configured to move between a small test tube position (i.e., at rest position) and a large test tube position (i.e., deflected position). The fixed portion 130b can include a recess sized large enough to allow the extraction needle 25 to pass through without creating an obstruction and prevents the test tube 39 from moving downward (e.g., when the extraction needle 25 is removed from the test tube cap 41).

The rotating portion 130a includes a spring mechanism that allows the rotating portion 130a to automatically return to an "at rest" position when released from a deflected position. During operation, when a test tube 39 is present in the inverting mechanism 47, the test tube stop 130 can rotate to temporarily secure the test tube 39 during fluid extraction. As shown in FIG. 5F, when a shorter test tube (e.g., a 75 mm long test tube) is being processed, the rotating portion 130a can remain in its at rest position to properly secure the shorter test tube.

Figure 5G:
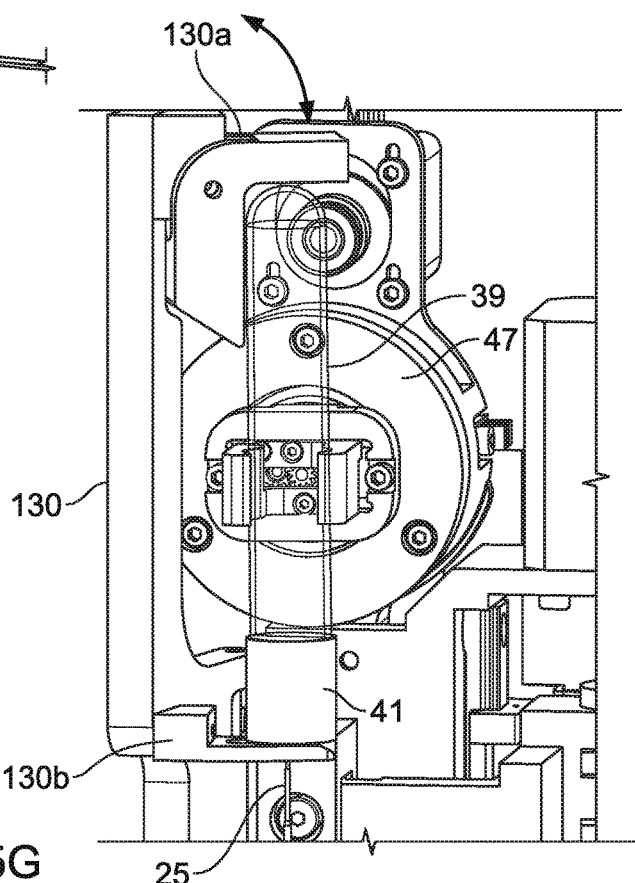
FIG. 5G is a perspective view of the test tube stop of FIG. 5F in a closed position securing a large test tube.

As shown in FIG. 5G, the test tube stop 130 can be used without modification to also secure a longer test tube (e.g., a 100 mm long test tube). As shown, when a longer test tube 39 is present in the inverting mechanism 47 and the test tube stop 130 approaches the test tube 39, the lower member of the rotating portion 130a, which can contact the top of a smaller test tube when a smaller test tube is present in the inverting mechanism 47, can contact the side of the larger test tube 39 (shown in FIG. 5G). Due to the lower member contacting the side of the test tube 39, the rotating member 130b rotates downward as it approaches the test tube 39 so that an upper member of the rotating portion moves into a position to secure the larger test tube 39 during penetration and exit of the extraction needle 25 within the test tube cap 41. After fluid extraction, the test tube stop 130 can move away from the test tube 39 so that the test tube 39 can be rotated upright for removal from the inverting mechanism 47. As the test tube stop 130 moves away from the test tube 39, the spring mechanism can cause the rotating portion 130a to return to its at rest position so that it can possibly receive a shorter or longer test tube in subsequent processing.

In some implementations, since the extraction needle 25 extracts the sample while the extraction needle 25 is pointed upward, it would typically be rotated to provide the sample to the sample vessel 35 (e.g., to point downward). One or more of various types of mechanisms (e.g., electric motors, electromagnetic devices, pneumatic actuators, leadscrews, and/or cam devices) can be used to rotate and position the extraction needle 25.

Figure 6:
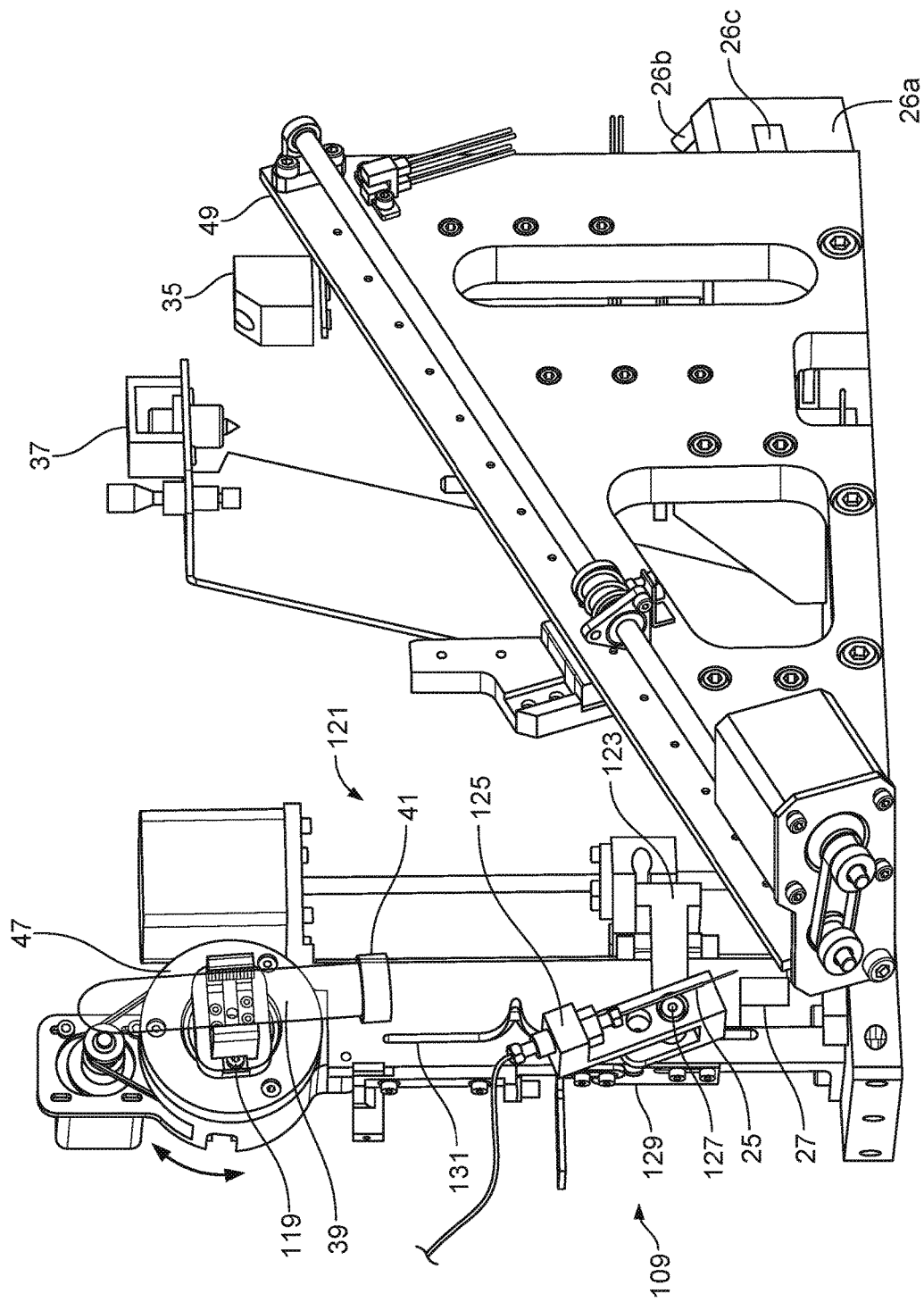
FIG. 6 is a perspective view of an inverting mechanism rotating a test tube to a position for fluid extraction.

As shown in FIG. 4 (and in greater detail in FIGS. 6-9), in some implementations, an electric motor and leadscrew can be used to translate the extraction needle 25 up and down while a cam mechanism can be used to provide rotation. To provide translation, the extraction needle 25 can include a non-rotating member 123 that acts as a leadscrew nut, translating along the leadscrew as it is rotated by the electric motor. As shown in FIG. 6, to provide rotation, the extraction needle rotating mechanism 121 can include the non-rotating member 123 connected to a rotating member 125 using a fastener at a pivot location 127. The rotating member 125 includes a pin 129 that is mounted at an off-center position with respect to a central axis of the pivot location 127 and moves along a profiled slot 131 to rotate the extraction needle 25 (e.g., 180° around a horizontal axis).

When the extraction needle 25 is at a most downward location (e.g., away from the inverting mechanism 47) and is pointed downward (e.g., away from the inverting mechanism 47), the pin 129 is in the slot 131 at a position above the non-rotating member 123 (e.g., the pin 129 is closer to the inverting mechanism 47 than the non-rotating member 123). As the leadscrew rotates and translates the extraction needle 25 upward, the pin 129 moves along the slot, following the profile of the slot. The slot 131 is shaped such that the motion of the pin 129 relative to the pivot location 127 causes the extraction needle 25 to rotate. At a particular location along the slot 131 profile, the pin 129 momentarily stops moving upward and the center axis of the pivot passes the center axis of the pin 129 in the upward direction, allowing the continued relative motion of the pin 129 and the pivot to cause the extraction needle 25 to continue to rotate upwards until the pivot location 127 is directly above the pin 129 and the extraction needle 25 is pointing upward.

With the extraction needle 25 pointed upward, the needle can be translated upward to pierce the cap 41 and to be inserted into the test tube 39 to extract a sample. As shown in FIG. 7, once the extraction needle 25 barely penetrates the test tube cap 41 and comes in contact with the sample, a portion of the sample can be withdrawn into the extraction needle 25 using the pneumatic or hydraulic techniques described herein, including the use of an air bubble or gap between the sample and the hydraulic fluid, e.g., a buffer fluid. The amount of sample withdrawn into the extraction needle 25 can vary depending on the analysis system in which the sample will be used. In some implementations, the extraction needle 25 can extract 10-50 microliters (e.g., 15, 20, 25, 30, 35, 40, or 45 microliters, e.g., 10 to 30 or 35 microliters) of the sample from the test tube 39. Samples can be removed while the test tube 39 is inverted in this manner even if the test tube 39 does not contain a minimum amount of sample that would be required if the extraction needle 25 were inserted from the top to contact the sample and the test tube were being held upright.

As shown in FIG. 8, once the sample portion is withdrawn and contained in the extraction needle 25, the extraction needle 25 can be removed from the test tube 39 by translating the extraction needle 25 downward. In some implementations, due to the design of the test tube cap 41 and the material it is made of, as the extraction needle 25 is removed from the test tube 39, the test tube cap 41 is able to automatically seal punctures created by the extraction needle 25. As discussed above, as the extraction needle 25 translates downward a cam device (e.g., the off-center mounted pin 129 moving in the slot 131) causes the extraction needle 25 to rotate 180° such that the extraction needle 25 containing the sample portion is pointed downward.

As shown in FIG. 8, in some implementations, the downward pointed extraction needle 25 can be moved further downward to dispense the sample portion extracted from the test tube 39 into a sample vessel 35. In such implementations, the sample vessel 35 can be moved along the track 49 to be positioned under the extraction needle 25 (e.g., the sample extraction position) to receive the sample portion. To dispense the sample into the sample vessel 35, pressure can be applied to the fluid system using the fluid pump 26b such that the buffer fluid can move in the extraction needle 25 and attached tubing to move the air bubble between the buffer fluid and the sample, and thus forcing the sample from the extraction needle 25 into the sample vessel 35. In some implementations, all of the sample portion contained in the extraction needle 25 can be dispensed into the sample vessel 35. In some cases, the amount dispensed can be between 10-50 microliters (e.g., 10 to 30 microliters, e.g., 10, 15, 20, 25, 30, 35, 40, or 45 microliters).

Once the sample portion is dispensed into the sample vessel 35, the extraction needle 25 can move upward to prevent any alignment problems (e.g., so that the sample vessel 35 can move along the track 49 without interference from the extraction needle 25).

In some implementations, instead of the gripping device 103 removing a sample container 39, such as a test tube, from a test tube rack 45 for processing a fluid contained therein, an operator can manually provide a test tube 39 to a fluid analysis system so that the analysis system can process the fluid contained therein. In such implementations, the fluid analysis system can include a door or opening that can open to receive the test tube and fluid. FIG. 5H shows an open mode port aspirator 140 in a stowed position that can be used to extract such samples from test tubes and provide the samples to the sample preparation system for processing. As shown in FIG. 5H, the open mode port aspirator 140 can be mounted to an xyz robot of the gripping device 103. The open mode port aspirator 140 can include an aspirator probe 142 having a seal 144 (e.g., tapered conical seal) and can be connected to deployment mechanism 146 (e.g., a four-bar linkage) to deploy the aspirator probe 142 between a stowed position (shown in FIG. 5H) and a deployed position (shown in FIG. 5I).

As shown in FIGS. 5H and 5I, the deployment mechanism 146 can include a device to secure the aspirator probe in either the stowed position or the deployed position, such as a two-position spring 148 connected to the deployment mechanism 146. As shown in FIG. 5J, in addition to the four-bar linkage that deploys the aspirator probe 142 outward radially, the deployment mechanism 146 can also move the aspirator probe 142 along a semi-circular path (e.g., to swing the aspirator probe 142 along an arcuate path). To move the aspirator probe 142 along the arcuate path, the deployment mechanism 146 can include a hinge 150 that can be operated by an arm of the xyz robot, which moves the gripping device 103. The hinge 150 can further include a magnet set 152 to further secure the open mode port aspirator 140 and keep the hinge 150 closed while in a stowed position.

Once the aspirator probe 142 is in a fully deployed position (e.g., positioned in an opening of the fluid analysis system), an operator can position an uncapped test tube having a sample disposed therein around the aspirator probe 142. In some cases, the test tube can positioned so that a top surface of the test tube is seated along the tapered conical seal 144 to prevent spilling of the sample contained therein during aspiration. In some cases, the aspirator probe 142 can be configured to reach the bottom of most standard test tubes to help ensure that a sample is removed from a test tube, even when the test tube contains little fluid. However, full seating of the test tube along the tapered conical seal 144 is typically not required for operation. Similar to the other fluid handling devices of the sample preparation system (e.g., the fluid extraction device and sample applicator) the aspirator probe 142 can be connected to a buffer fluid system used to withdraw the fluid from the test tube into the aspirator probe 142. Once the sample is withdrawn into the aspirator probe 142, the operator can remove the test tube from the aspirator probe area. With the sample withdrawn and the test tube removed, the xyz robot can translate the aspirator probe 142 to a position above a sample vessel so that the sample can be dispensed into the sample vessel for processing. Once in the sample vessel, the subsequent processing of the sample is generally the same as if the sample were withdrawn using the extraction device.

Once the sample is dispensed from the aspirator probe 142, the xyz robot can translate the aspirator probe to an aspirator probe wash station 142*a* (shown in FIG. 5J). In some implementations, the aspirator probe wash station 142*a* can be a device in which the entire aspirator probe 142 can be inserted and sealed using the tapered conical seal 144. A reason for having a separate aspirator probe washing station (i.e., as opposed to using the extraction needle wash station) is because since the aspirator probe can be inserted into test tubes containing a wide range of fluid levels, it is generally uncertain what portion of the outer surface of the aspirator probe 142 must be cleaned, and therefore using a wash station that can clean the entire outer surface of the aspirator probe 142 can reduce contamination of subsequent samples.

Once the aspirator probe 142 is cleaned, the deployment mechanism 146 can move the aspirator probe 142 back to a stowed position where it can remain until it is deployed for subsequent open mode port processing.

Figure 16A:
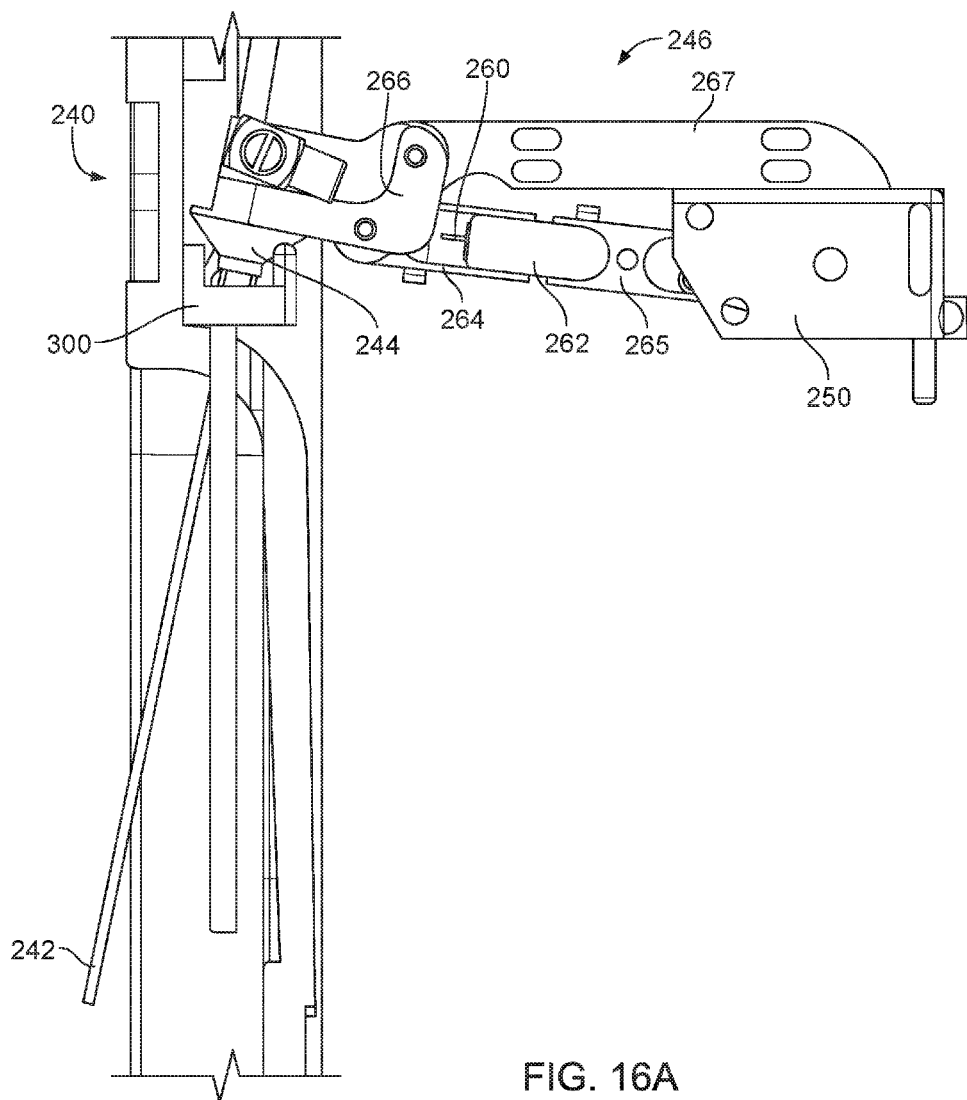
FIG. 16A is a schematic diagram of an open mode port aspirator in a deployed position.

FIG. 16A shows another implementation of an open mode port aspirator 240. In FIG. 16A, aspirator 240 is shown in an extended position such that a test tube or other sample container can be positioned in proximity to the aspirator, and the sample within the container can be drawn into the aspirator. Aspirator 240 is mounted to an xyz robot of gripping device 103, and includes an aspirator probe 242 having a seal 244 (e.g., tapered conical seal). Aspirator 240 is connected to deployment mechanism 246 with a five-bar linkage to deploy the aspirator probe 142 between a stowed position and the deployed position shown in FIG. 16A.

In addition to the five-bar linkage that deploys the aspirator probe 242 outward radially, deployment mechanism 246 can also move the aspirator probe 242 along a semi-circular path (e.g., to swing the aspirator probe 242 along an arcuate path). To move the aspirator probe 242 along the arcuate path, the deployment mechanism 246 can include a hinge 250 that can be operated by an arm of the xyz robot, which moves the gripping device 103. The hinge 250 can further include a magnet set (not shown in FIG. 16A) to further secure the open mode port aspirator 240 and keep the hinge 250 closed while in a stowed position.

Figure 16B:
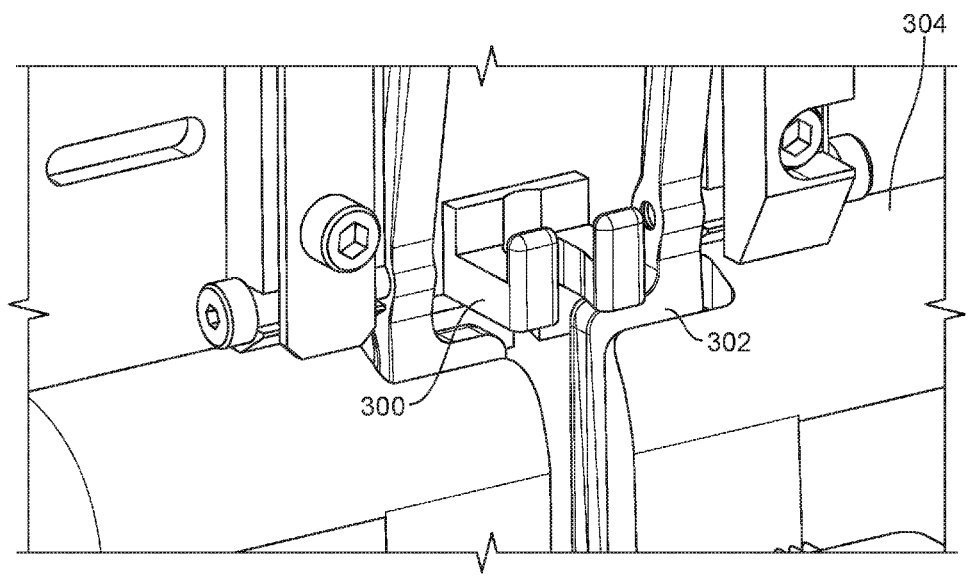
FIG. 16B is a perspective view of a pivot block for rotating an aspirator probe to a deployed position.
Figure 16C:
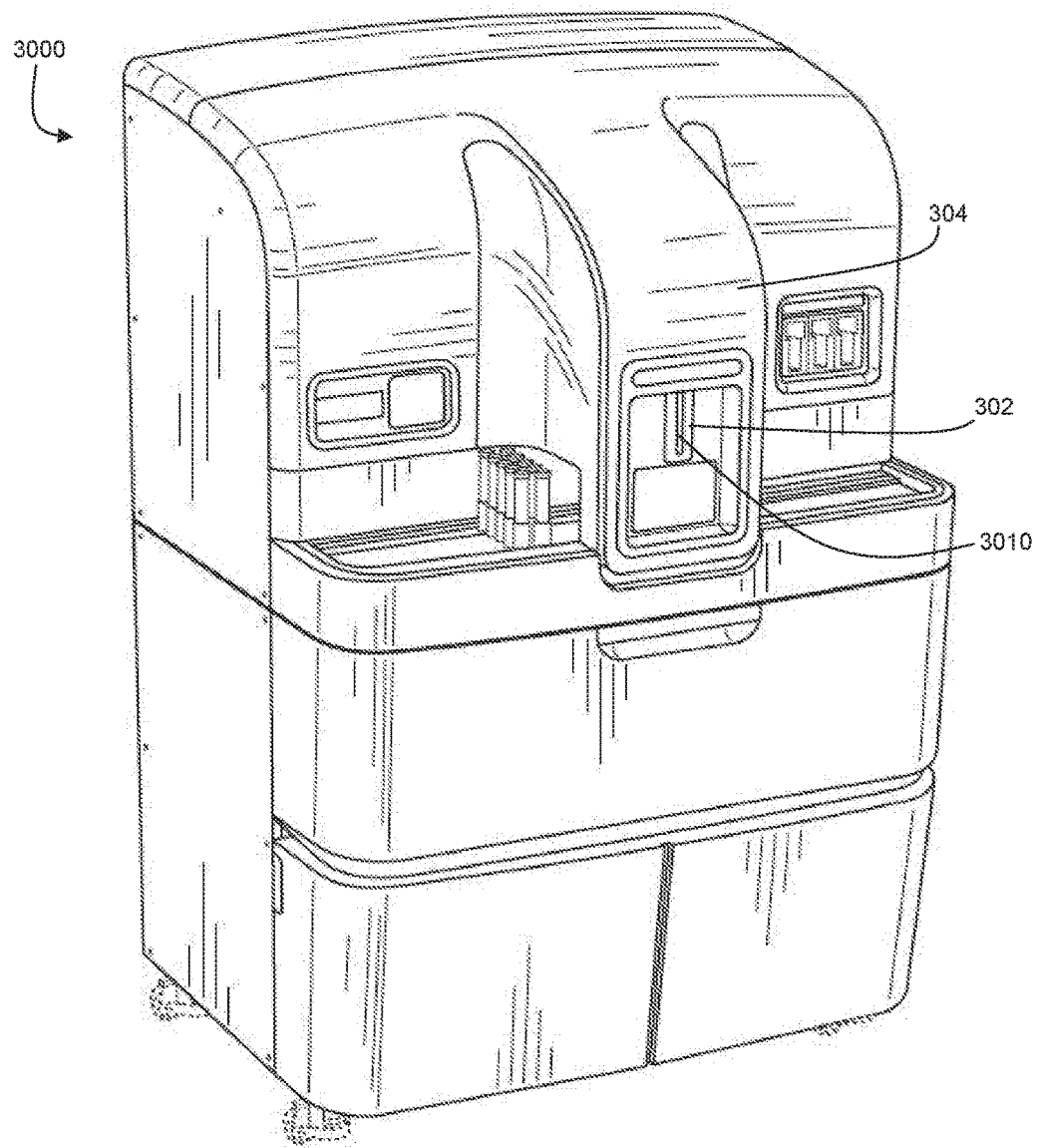
FIG. 16C is a perspective view of an automated blood analyzer.

Within the five-bar linkage, lower links 264 and 265 are connected by guide block 262, which keeps links 264 and 265 aligned with one another. Upper links 266 and 267 are directly connected and constitute the other members of the five-bar linkage. To move aspirator probe 242 into a deployed position, the xyz robot translates gripping device 103 so that aspirator probe 242 is inserted into an opening in U-shaped pivot block 300, which is supported by paddle 302 and hood cover 304 as shown in FIG. 16B. FIG. 16C is a perspective view of a blood analyzer 3000, and shows the positions of paddle 302 and hood cover 304 in greater detail. As seal 244 comes into contact with the surface of pivot block 300, seal 244 and aspirator probe 242 rotate outward within the opening so that aspirator probe 242 is in the deployed position shown in FIG. 16A. Individual links in the five-bar linkage move passively with respect to one another as aspirator probe 242 rotates. When the xyz robot translates gripping device 103 upward in FIG. 16A, aspirator probe 242 rotates inward toward a retracted position. The inward rotation of probe 242 is halted by external spring 260 when probe 242 is fully retracted. Referring again to FIG. 16C, recess 3010 is contiguous with the opening in pivot block 300 so that aspirator probe 242 can be fully deployed and retracted, as shown in FIG. 16A.

With aspirator probe 242 in a fully deployed position (e.g., positioned in an opening of the fluid analysis system), an operator can position an uncapped test tube having a sample disposed therein around the aspirator probe 242. In some cases, the aspirator probe 242 can be configured to reach the bottom of most standard test tubes to help ensure that a sample is removed from a test tube, even when the test tube contains little fluid. Similar to the other fluid handling devices of the sample preparation system (e.g., the fluid extraction device and sample applicator) the aspirator probe 242 can be connected to a buffer fluid system used to withdraw the fluid from the test tube into the aspirator probe 242. Once the sample is withdrawn into the aspirator probe 242, the operator can remove the test tube from the aspirator probe area. With the sample withdrawn and the test tube removed, the xyz robot can translate the aspirator probe 242 to a position above a sample vessel so that the sample can be dispensed into the sample vessel for processing.

Once the sample is dispensed from the aspirator probe 242, the xyz robot can translate the aspirator probe to an aspirator probe wash station and aspirator probe 242 can be cleaned as disclosed above. After cleaning, aspirator probe 242 can be moved by deployment mechanism 246 to a stowed position where it can remain until it is deployed for subsequent open mode port processing.

Referring back to FIG. 4, the sample vessel 35 is a vessel having an arcuate inner surface (e.g., spherical, elliptical, or similar shaped surface) used to carry (e.g., contain or support) a sample (e.g., a fluid sample) as it is transported to various components of the system (e.g., under the extraction needle 25, under the diluent needle, under the sample applicator 31). In some implementations, the sample vessel 35 can contain a volume of approximately 10 microliters to 100 microliters (e.g., 70 microliters). As discussed above, in some implementations, the sample vessel 35 is typically made of an inert, smooth, non-porous material that can reduce wetting of fluids (e.g., sample fluids) contained the sample vessel 35 so that the fluids are expected to flow more easily to the bottom of the sample vessel 35. In some implementations, the sample vessel 35 can be formed of various materials, such as different types of plastics (e.g., PTFE, acetalhomopolymer, acetalcopolymer, acrylic, Ultem®, Teflon®, Delrin®, or Noryl®), glasses, and/or metal materials.

Figure 13:
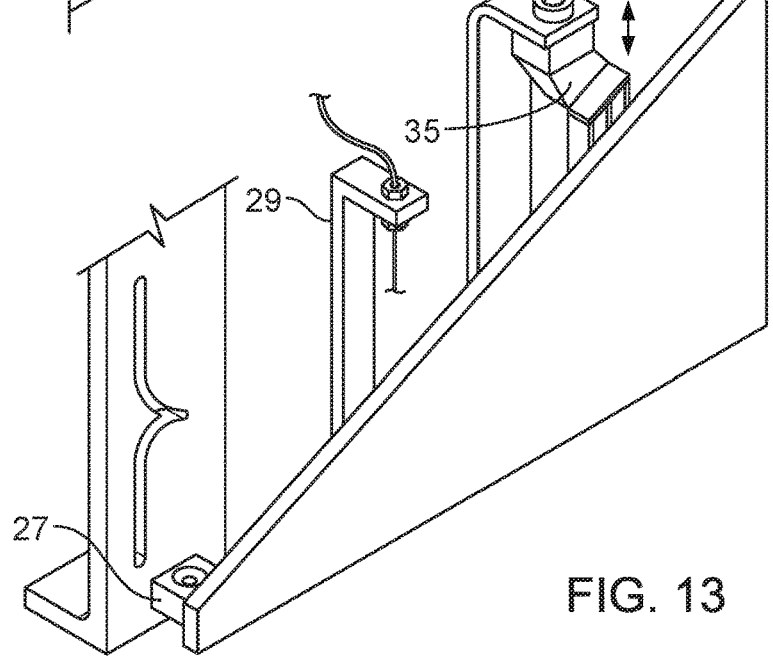
FIG. 13 is a perspective view of the sample vessel of FIG. 8 translating to engage a sample vessel wash system.
Figure 14:
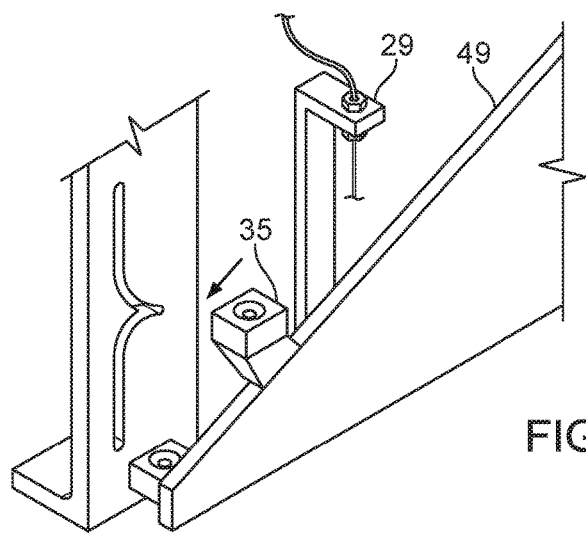
FIG. 14 is a perspective view of the sample vessel of FIG. 8 translating back to the sample extraction position under the extraction needle.

The sample vessel wash system 37 can include a fluid delivery system to provide a wash fluid (e.g., an embodiment of the combined buffer and wash fluid solution described herein) to the sample vessel 35 to clean the sample vessel 35 and to flush any residual sample fluids from the sample vessel 35. In some implementations, the sample vessel wash system 37 can include a vacuum conduit used to remove any fluids dispensed into the sample vessel 35 by the fluid delivery system. As shown in FIG. 13, in some implementations, the sample vessel wash system 37 can be rigidly mounted and the sample vessel 35 can have an additional translating device to move the sample vessel 35 to the sample vessel wash system 37 for cleaning. In other implementations, the sample vessel wash system 37 can be mounted on a translating device so that the sample vessel wash system 37 can be moved to contact and clean the sample vessel 35. As shown in FIG. 13, the sample vessel wash system can be mounted between the sample applicator 31 and the sample modification system 29 so that as the sample applicator 21 applies a sample to a sample carrier 55, the sample vessel 35 can move along the track 49 towards the sample extraction position and stop along the way to clean the wash cup 35 to prepare to receive a next sample. As shown in FIG. 14, after being cleaned of residual sample fluids in a sample vessel wash system 37, the sample vessel 35 can be returned to the sample extraction position to receive and carry a next sample.

Figure 17:
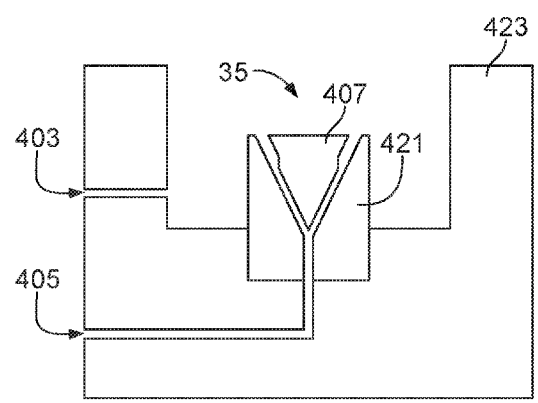
FIG. 17 is a cross-sectional view of a sample vessel.

To avoid contaminating various components within the system and jeopardizing the accuracy of blood analysis results, it is important to clean sample vessel 35 as thoroughly as possible between samples. FIG. 17 shows another embodiment of a sample vessel 35 and wash system 37. In FIG. 17, sample vessel 35 includes a mixing cup 421 and a base 423. Wash system 37 includes channels 403 and 405 extending through sample vessel 35, and a cap 407 dimensioned to fit into the conical opening in cup 421. After a sample has been withdrawn from cup 421, a small portion of the sample typically remains on the interior walls of cup 421. To clean the cup, a wash solution is deposited into cup 421 and the solution (with remnants of the sample) is partially drawn out through channel 405 to rinse the interior cup surface. The, cap 407 is lowered into cup 421. The wash solution and sample remnants that remain within cup 421 are compressed against the interior surface of cup 421. A portion of this liquid is again drawn out through channel 405. The remaining portion is forced upward along the interior surface of cup 421 and spills over into base 423 from which it is drawn out through channel 403. Cap 407 is then withdrawn from the opening in cup 421, leaving the interior surface of the cup clean.

Cup 421 can be formed from a variety of materials. In some implementations, cup 421 is formed from a hard material such as quartz. The hardness of quartz (or other material) should be sufficiently great such that the surface of cup 421 is not scratched by extraction syringes that deposit or remove fluids from cup 421, and the absence of scratches on the cup surface prevents formation of pockets of fluids at the surface. Moreover, biological materials generally have low adherence to quartz surfaces, so that the interior surface of cup 421 can be easily cleaned according to the steps disclosed above. Without wishing to be bound by theory, it is believed that the high surface energy of quartz helps to prevent the adherence of biological materials and solutions. Other materials with large surface energies can also be used to form cup 421, including Teflon®, stainless steel, and PTFE.

Typically, cup 421 is a permanent component of a blood analyzer. However, in some implementations, cup 421 is a disposable component that can be discarded after one or more samples have been deposited therein. Disposable cups 421 can be formed of materials such as various plastics to reduce costs.

Referring back to FIG. 4, the sample vessel movement mechanism 33 is provided to move the sample vessel 35 to each of the various positions associated with each of the components of the system (e.g., under the extraction needle 25, under the modification system 29, and under the sample applicator 31). The sample vessel movement mechanism 33 can include a track 49 (e.g., a sliding track) on which the sample vessel 35 can smoothly translate and be moved. The movement of the sample vessel 35 on the track 49 can be controlled by various devices, such as electromechanical devices (e.g., an electric motor connected to a leadscrew), an electromagnetic device, or a pneumatically powered actuator. In some implementations, the track 49 can have the device used to move and control the motion of the sample vessel 35 built into the track 49, such as a linear actuator (e.g., a pneumatic linear actuator or an electromechanical linear actuator).

As shown in FIG. 4, in some implementations, a sample preparation system 21 can include a sample modification system 29 (e.g., a diluent system) to modify the sample prior to the sample being provided to the analysis system (e.g., prior to reaching the applicator position). A diluent system can include a diluent conduit 53 (e.g., a section of tubing, a syringe tip, a pipette, or a needle) connected to a fluid delivery system to provide a diluent fluid to the sample. In some implementations, a diluent fluid for a blood sample can include salt solutions (e.g., "physiological saline" or Plasmalyte™) protein solutions (e.g., bovine albumin, Plasmanate®) and/or synthetic solutions (e.g., Ficoll®, Dextran™, or other polysaccharides). As shown in FIG. 9, during use, a sample vessel 35 can be translated along the track 49 to a position under the modification system 29 (e.g., to the diluent position) to receive a portion of diluent. The amount of diluent fluid dispensed into a blood sample can vary based on the sample. In some cases, diluent fluid can be dispensed into a sample, e.g., a blood sample, to achieve a diluent fluid to blood ratio ranging from 0:1 (no dilution) to 10:1 (diluent: blood). When analyzing whole blood, a dilution of 2 parts blood to 1 part diluent can be used. In some implementations where the sample is blood, 10 microliters to 150 microliters (e.g., 25, 30, 40, 50, 75, 100, or 125 microliters) of diluent can be dispensed into the sample vessel 35 to mix with a volume of sample of 10 to 35 microliters (e.g., 15, 20, 25, or 30 microliters).

Referring back to FIG. 4, the sample applicator 31 can include an application conduit 57 (e.g., a section of tubing, a syringe tip, a pipette, or a needle) connected to a buffer fluid handling system. Similar to the extraction needle 25, the buffer fluid handling system connected to the application conduit 57 can be used to withdraw the sample from the sample vessel 35 into the application conduit 57 and then to dispense the sample onto a sample carrier (e.g., a glass slide) of the analysis system. The sample applicator 31 can further include a translating device 32 such that the application conduit 57 can move in multiple directions when applying the sample.

Figure 11:
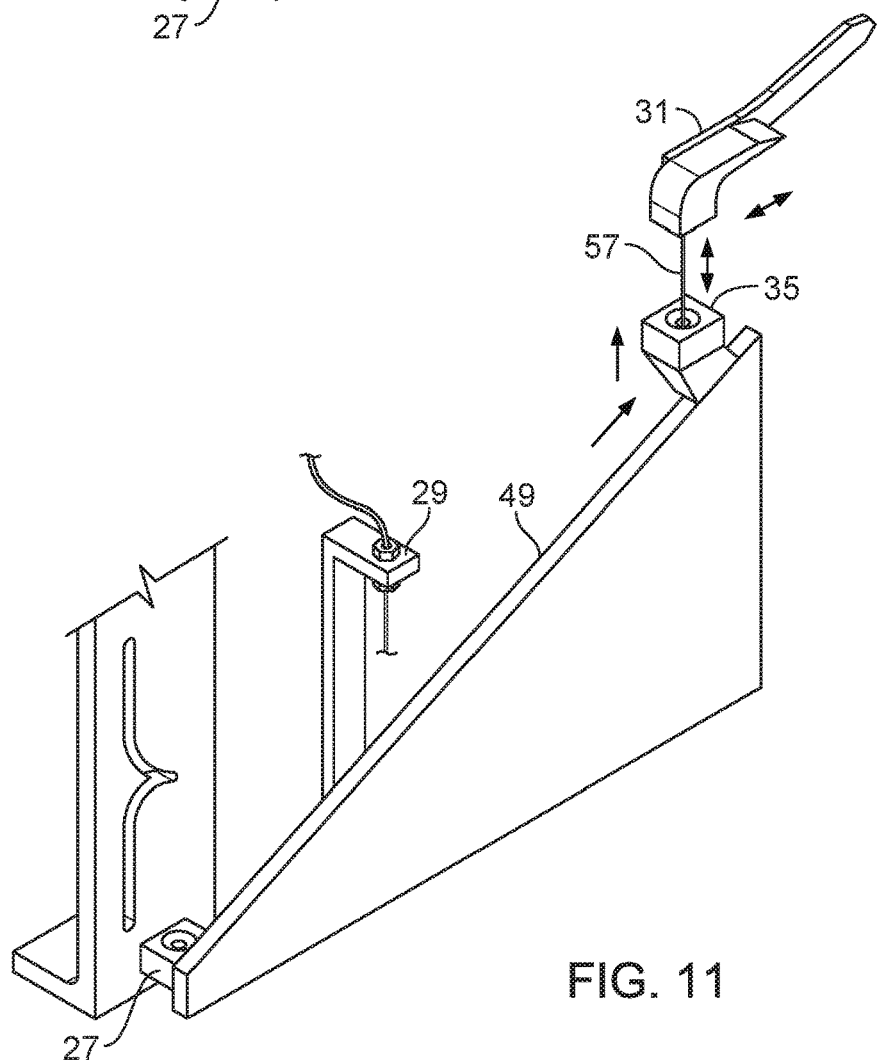
FIG. 11 is a perspective view of the sample vessel of FIG. 8 translating to a sample application position under an application conduit.

As shown in FIG. 11, in some implementations, the sample applicator 31 (e.g., the application conduit 57) can be translated downward and inserted into the sample vessel 35 to withdraw the sample contained in the sample vessel 35. In some implementations, the application conduit 57 removes the entire sample, or a substantial majority of the sample. In certain implementations, the application conduit 57 can withdraw a sample having a specific volume of between 0.1-50 microliters (e.g., 0.08 microliters, 1.0 microliters, 30 microliters). Similar to the operation of the extraction needle 25 extracting the sample using the fluid system, the application conduit 57 can withdraw the sample into the application conduit 57 by changing the pressure of the buffer fluid (e.g., using a fluid pump 26b to reduce the buffer fluid pressure to create a vacuum in the application conduit 57) to cause the sample to flow into the application conduit 57.

Figure 12:
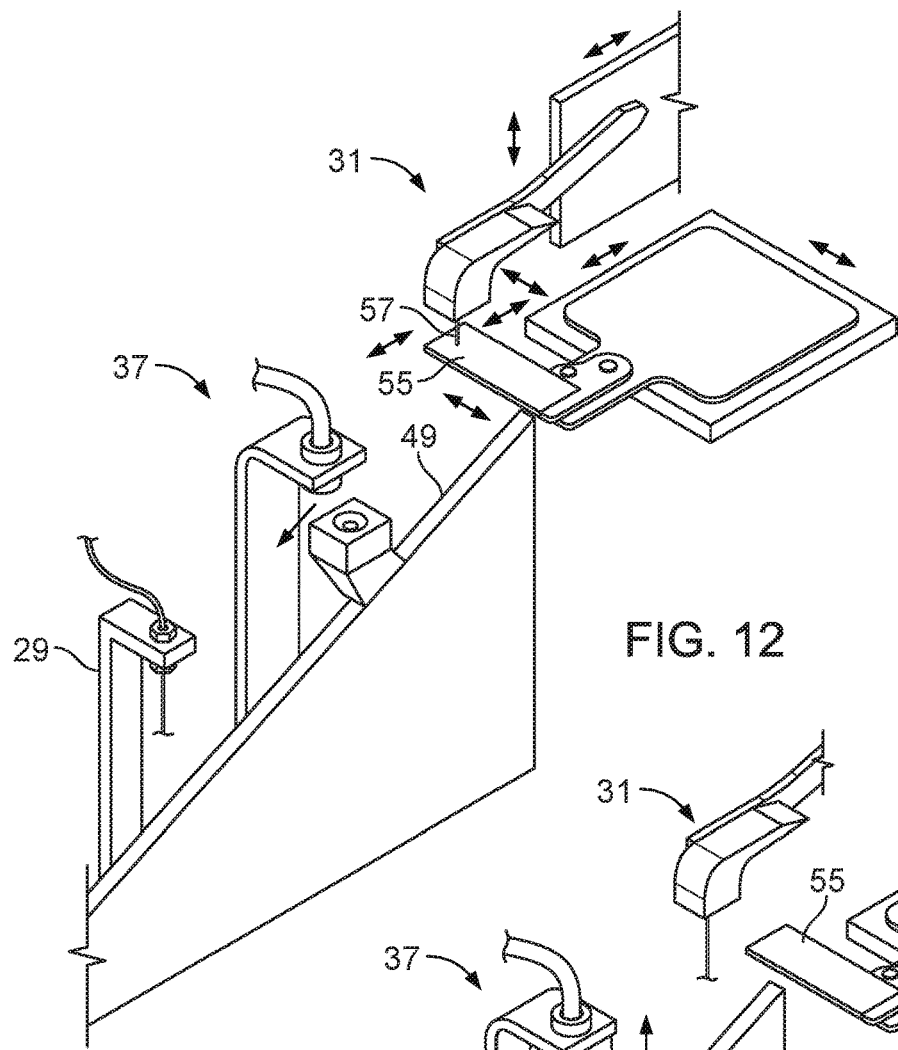
FIG. 12 is a perspective view of the application conduit of FIG. 11 applying a sample to a sample carrier.

As shown in FIG. 12, once the sample is withdrawn into the application conduit 57, it can be dispensed onto a sample carrier 55 (e.g., a glass slide) as the sample vessel 35 moves along the track 49 away from the sample application position. In some implementations, the sample can be dispensed using the same hydraulic, e.g., buffer, fluid system used to withdraw the sample into the application conduit 57. In some implementations, the application conduit 57 can be moved relative to the glass slide 55 to produce various patterns of the sample fluid onto the glass slide 55. Such patterns can include a serpentine or raster pattern, a continuous spiral pattern, a pattern of multiple concentric circles, and/or a pattern of multiple parallel lines. In some cases, a blood sample can be applied to the glass slide to form a monolayer of a sample containing cells, such as a sample of blood (e.g., a layer of cells approximately one cell thick). In some implementations, the height of the sample layer applied can range from less than 1 micron to 10 microns or more. The sample can be applied in one continuous flow or in multiple flows that are spaced apart or are applied side-by-side or even contacting each other.

Although samples can be dispensed at various flow rates based on the type of sample and the desired sample pattern formed on the glass slide 55, in some implementations, an application conduit 57 having an inner diameter of 300 microns can provide a sample flow rate of 0.1 microliters per second. More generally, the inner diameter of application conduit 57 can be in a range from 200 microns to 650 microns inclusive (e.g., between 200 microns and 400 microns, between 300 microns and 400 microns, between 400 microns and 650 microns, between 500 microns and 650 microns).

In some implementations, the entire sample is dispensed from the application conduit 57 onto the glass slide. In some implementations, the flow rate of the sample dispensed from the application conduit 57 can be 0.1 microliters per second while the application conduit 57 is moving at a speed of 30 millimeters per second over the glass slide surface at a height of about 5 to 100 microns, e.g., 15 to 50, 10 to 15, 20 to 40, or 5 to 15 microns, about 12 microns. In some implementations, when dispensing a sample of undiluted blood, the flow rate through the application conduit 57 can be approximately 0.04 microliters per second, e.g., 0.02 to 0.10, 0.02 to 0.05, or 0.03 to 0.04 microliters per second, while the application conduit 57 is moving at a speed of about 50 millimeters per second, e.g., 10 to 100, 20 to 80, 30 to 70 millimeters per second, while the application conduit 57 is at a height of 10, 12, 14, 15, 20, or 25 microns from the slide surface.

Referring back to FIG. 4, in some implementations, the sample preparation system can include multiple wash cups (e.g., an extraction needle wash cup 27 and a sample applicator wash cup 28) that can operate in substantially the same way. Although the following explanation is directed towards one particular wash cup (e.g., the extraction needle wash cup 27) and references components and/or features of the extraction needle wash cup 27, the structure and operation of other wash cups in the system (e.g., the sample applicator wash cup 28) are substantially the same as described.

The extraction needle wash cup 27 can include an inner basin 27a and an outer basin 27b that substantially surrounds the inner basin 27a. The inner basin 27a can be shaped (e.g., a substantially cylindrical and/or half spherical inner basin) to receive a fluid dispensing member portion (e.g., the extraction needle 25 and/or the application conduit 57) and can be designed to be slightly larger (e.g., 25% to 100% larger) than the outer diameter of the member portion (e.g., the extraction needle 25 or the application conduit 57) to be inserted into the wash cup 27 and can have a substantially rounded bottom. The outer basin 27b can include a fluid output device 27c (e.g., a drain or fluid suction device). The inner basin 27a and the outer basin 27b can be designed such that when a member is inserted into the wash cup 27, the buffer fluid can be dispensed from the member to wash the inner surface of the member. When the buffer fluid exits the member portion, the rounded shape of the inner basin 27a can cause the fluid to continuously flow upwards along the outer surface of the member as the wash cup fills with the fluid. The continuous flow of buffer fluid pumped using the pump 26b from the fluid reservoir 26a through the member portion and directed by curved bottom surface of the wash cup 27 allows the inserted member portion to flush residual fluid samples remaining on the inner surface and/or the outer surface while minimizing the likelihood of cross-contamination of samples.

Cross-contamination can be minimized because none of the wash fluid pumped from the member portion during rinsing/cleaning typically re-enters the member. After the buffer fluid flows along the outer surface of the member, it can flow over an upper edge of the inner basin 27a and into the outer basin 27b. The contaminated fluid in the outer basin 27b can be removed by the fluid output device 27c of the outer basin 27b and disposed into a waste reservoir. After a certain amount of buffer fluid is dispensed from the member, the fluid system can stop the flow of the buffer fluid and withdraw the buffer fluid back into the member to create an air pocket in the member such that the air pocket can serve as a barrier between the buffer fluid and future fluids withdrawn into the member (e.g., a next portion of sample).

In some embodiments, wash cup 27 (and wash cup 28) can be implemented as described above for sample vessel 35. For example, wash cup 27 can include an insert with a high surface energy (e.g., formed of a material such as quartz) supported by a base. Wash cup 27 can have a geometry similar to that shown in FIG. 17 for vessel 35, and can be automatically cleaned in a similar manner.

Figure 10:
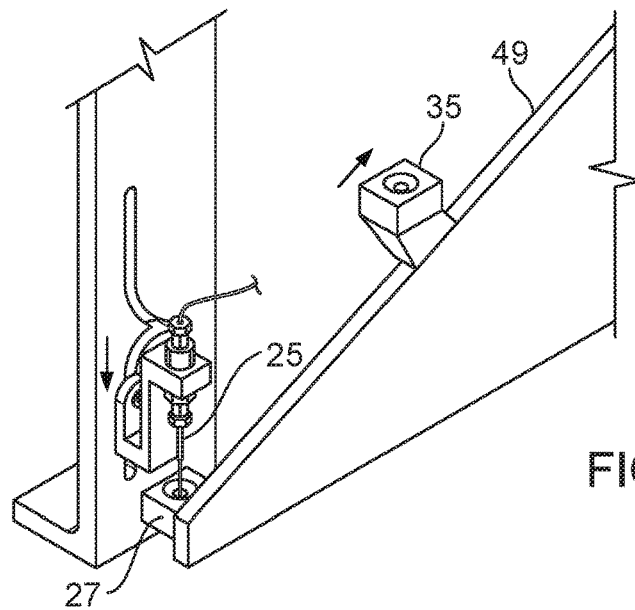
FIG. 10 is a perspective view of the extraction needle of FIG. 7 being inserted into a wash cup.
Figure 15:
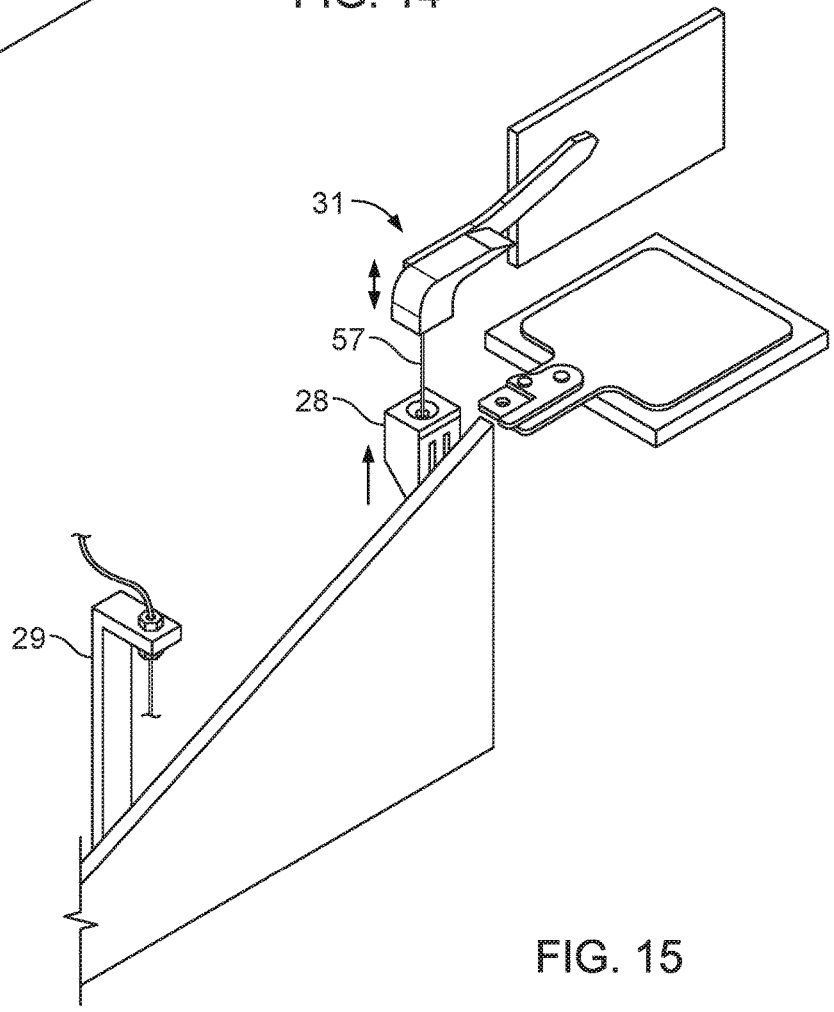
FIG. 15 is a perspective view of the application conduit inserted in a wash cup.

As shown in FIG. 10, the extraction needle 25 can be translated down and inserted into the extraction needle wash cup 27 to be cleaned as the sample vessel 35 is translating along to track 49 away from the sample application position. Similarly, as shown in FIG. 15, as the sample vessel moves along the track 49 away from sample applicator 21, the application conduit 57 can be inserted into the sample applicator wash cup 28 and cleaned by dispensing buffer fluid from the application conduit 57 such that the buffer fluid washes the inner surface and outer surface of the application conduit 57. Once cleaned in a wash cup, the fluid handling devices (e.g., the extraction needle 25 and the application conduit can handle a next sample).

With all of the components of the sample preparation system 21 cleaned, a next sample from the same or a next test tube 39 can be prepared for analysis Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of dispensing a sample, the method comprising:
    receiving a sample container containing a volume of a fluid sample, wherein the sample container comprises a sealing member that seals an opening in the sample container;
    orienting the sample container so that an exterior surface of the sealing member faces downward toward a sample carrier, and the fluid sample contacts and is retained within the sample container by the sealing member;
    removing a portion of the fluid sample from the sample container by inserting an extraction device through the sealing member with the fluid sample contacting the sealing member; and
    dispensing the portion of the fluid sample onto the sample carrier.

2. The method of claim 1, wherein the extraction device is operated by a fluid system, and wherein fluid of the fluid system is separated from the sample portion by an air pocket within the extraction device.

3. The method of claim 1, wherein the fluid sample comprises blood and sample carrier comprises a slide.

4. The method of claim 1, wherein orienting the sample container comprises inverting the sample container.

5. The method of claim 1, wherein orienting the sample container comprises rotating the sample container by an angle of at least a from a first orientation to a second orientation, and removing the portion of the fluid sample with the sample container in the second orientation.

6. The method of claim 5, wherein a is between 90 degrees and 180 degrees.

7. The method of claim 5, wherein a is more than 360 degrees.

8. The method of claim 1, further comprising inserting the extraction device through the sealing member such that a portion of the extraction device extends into an interior volume of the sample container and contacts only the fluid sample within the interior volume.

9. The method of claim 1, wherein the extraction mechanism comprises a needle.

10. The method of claim 1, further comprising:
    discharging the portion of the fluid sample from the extraction device into a sample vessel;
    removing the portion of the fluid sample from the sample vessel using a sample applicator; and
    dispensing the portion of the fluid sample onto the sample carrier using the sample applicator.

11. The method of claim 10, further comprising dispensing the portion of the fluid sample onto the sample carrier in at least one of a serpentine pattern, a raster pattern, a continuous spiral pattern, a pattern of multiple concentric circles, and a pattern of multiple parallel lines.

12. A system, comprising:
    a sample container carrier configured to receive a sample container containing a volume of a fluid sample, wherein the sample container comprises a sealing member that seals an opening in the sample container, and to orient the sample container so that an exterior surface of the sealing member faces downward toward a sample carrier and the fluid sample contacts and is retained within the sample carrier by the sealing member;
    an extraction mechanism comprising an extraction device, wherein the extraction mechanism is configured to insert the extraction device through the sealing member with the fluid sample contacting the sealing member to remove a portion of the fluid sample from the sample container; and
    a dispensing mechanism configured to dispense the portion of the fluid sample onto the sample carrier.

13. The system of claim 12, wherein the sample container carrier is configured to rotate the sample container from a first orientation in which the sample container is upright to a second orientation in which the sample container is inverted.

14. The system of claim 12, wherein the extraction mechanism is configured to insert the extraction device through the sealing member such that a portion of the extraction device extends into an interior volume of the sample container and contacts only the fluid sample within the interior volume.

15. The system of claim 12, further comprising a fluid control system connected to an interior channel of the extraction device and configured to remove the portion of the fluid sample from the sample container through the interior channel by controlling a fluid pressure of an auxiliary fluid in the interior channel.

16. A method of dispensing a sample, the method comprising:
  receiving a sample container containing a volume of a fluid sample, wherein the sample container comprises a sealing member that seals an opening in the sample container;
  orienting the sample container so that an exterior surface of the sealing member faces downward toward a sample carrier, and the fluid sample contacts and is retained within the sample container by the sealing member;
  removing a portion of the fluid sample from the sample container by inserting an extraction device through the sealing member with the fluid sample contacting the sealing member and withdrawing the portion of the fluid through an interior channel in the extraction device by controlling a fluid pressure in the interior channel; and
  dispensing the portion of the fluid sample onto the sample carrier.

17. The method of claim 16, further comprising controlling the fluid pressure in the interior channel by controlling a flow of an auxiliary fluid within the interior channel.

18. The method of claim 17, wherein the auxiliary fluid comprises a buffer solution.

19. The method of claim 16, wherein orienting the sample container comprises inverting the sample container.

20. The method of claim 16, wherein orienting the sample container comprises rotating the sample container by an angle of at least a from a first orientation to a second orientation, and removing the portion of the fluid sample with the sample container in the second orientation, wherein a is between 90 degrees and 180 degrees.

21. The method of claim 16, further comprising inserting the extraction device through the sealing member such that a portion of the extraction device extends into an interior volume of the sample container and contacts only the fluid sample within the interior volume.

22. A method of dispensing a sample, the method comprising:
  receiving a sample container containing a volume of a fluid sample, wherein the sample container comprises a sealing member that seals an opening in the sample container;
  orienting the sample container so that an exterior surface of the sealing member faces downward toward a sample carrier, and the fluid sample contacts and is retained within the sample container by the sealing member;
  rotating an extraction device from a first orientation in which a tip of the extraction device faces downward toward the sample carrier to a second orientation in which the tip of the extraction device faces away from the sample carrier;
  removing a portion of the fluid sample from the sample container by inserting the rotated extraction device through the sealing member with the fluid sample contacting the sealing member; and
  dispensing the portion of the fluid sample onto the sample carrier.

23. The method of claim 22, further comprising translating at least one of the extraction device and the sample container relative to one another to insert the extraction device through the sealing member.

24. The method of claim 22, wherein orienting the sample container comprises inverting the sample container.

25. The method of claim 22, wherein orienting the sample container comprises rotating the sample container by an angle of at least a from a first orientation to a second orientation, and removing the portion of the fluid sample with the sample container in the second orientation, wherein a is between 90 degrees and 180 degrees.

26. The method of claim 22, further comprising inserting the extraction device through the sealing member such that a portion of the extraction device extends into an interior volume of the sample container and contacts only the fluid sample within the interior volume.

* * * * *

UNITED STATES PATENT AND TRADEMARK OFFICE
CERTIFICATE OF CORRECTION

PATENT NO. : 10,345,205 B2
APPLICATION NO. : 15/450731
DATED : July 9, 2019
INVENTOR(S) : Brian J. McKeen et al.

It is certified that error appears in the above-identified patent and that said Letters Patent is hereby corrected as shown below:

In the Claims

Column 30, Line 21:
In Claim 5, delete "a" and insert -- $\alpha$ --, therefor.

Column 30, Line 24:
In Claim 6, delete "a" and insert -- $\alpha$ --, therefor.

Column 30, Line 26:
In Claim 7, delete "a" and insert -- $\alpha$ --, therefor.

Column 31, Line 46:
In Claim 20, delete "a" and insert -- $\alpha$ --, therefor.

Column 32, Line 2:
In Claim 20, delete "a" and insert -- $\alpha$ --, therefor.

Column 32, Line 37:
In Claim 25, delete "a" and insert -- $\alpha$ --, therefor.

Column 32, Line 41:
In Claim 25, delete "a" and insert -- $\alpha$ --, therefor.

Signed and Sealed this
Fifth Day of May, 2020

Andrei Iancu
*Director of the United States Patent and Trademark Office*